(12) United States Patent
Kageyama et al.

(10) Patent No.: US 10,485,894 B2
(45) Date of Patent: *Nov. 26, 2019

(54) FORMED SHEET PRODUCT AND HEMOSTATIC MATERIAL

(71) Applicants: TEIJIN LIMITED, Osaka-shi, Osaka (JP); TEIJIN PHARMA LIMITED, Chiyoda-ku, Tokyo (JP); THE CHEMO-SERO-THERAPEUTIC RESEARCH INSTITUTE, Kumamoto-shi, Kumamoto (JP)

(72) Inventors: Yukako Kageyama, Hino (JP); Kentaro Fujinaga, Hino (JP); Ayuko Yamaguchi, Hino (JP); Yusuke Akiyama, Hino (JP); Akitoshi Oono, Hino (JP); Susumu Honda, Hino (JP); Makoto Satake, Hino (JP); Hiroaki Kaneko, Hino (JP); Takayuki Imamura, Kikuchi (JP); Ryoichi Kawamura, Kikuchi (JP); Masaki Hirashima, Kikuchi (JP)

(73) Assignees: TEIJIN LIMITED, Osaka-shi, Osaka (JP); Teijin Pharma Limited, Chiyoda-ku, Tokyo (JP); KM BIOLOGICS CO., LTD., Kumamoto-shi, Kumamoto (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/399,117

(22) PCT Filed: May 13, 2013

(86) PCT No.: PCT/JP2013/063872
§ 371 (c)(1),
(2) Date: Nov. 5, 2014

(87) PCT Pub. No.: WO2013/172472
PCT Pub. Date: Nov. 21, 2013

(65) Prior Publication Data
US 2015/0151020 A1 Jun. 4, 2015

(30) Foreign Application Priority Data

| May 14, 2012 | (JP) | 2012-110391 |
| May 14, 2012 | (JP) | 2012-110392 |
| May 14, 2012 | (JP) | 2012-110393 |
| May 14, 2012 | (JP) | 2012-110394 |
| Jan. 11, 2013 | (JP) | 2013-003273 |

(51) Int. Cl.
| A61L 24/00 | (2006.01) |
| A61K 38/36 | (2006.01) |
| A61K 38/48 | (2006.01) |
| A61L 26/00 | (2006.01) |
| A61L 24/04 | (2006.01) |

(52) U.S. Cl.
CPC ........ *A61L 26/0066* (2013.01); *A61K 38/363* (2013.01); *A61K 38/4833* (2013.01); *A61L 24/0015* (2013.01); *A61L 24/0036* (2013.01); *A61L 24/0042* (2013.01); *A61L 24/043* (2013.01); *A61L 26/009* (2013.01); *A61L 26/0052* (2013.01); *A61L 26/0085* (2013.01); *A61L 2300/25* (2013.01); *A61L 2300/252* (2013.01); *A61L 2300/418* (2013.01); *A61L 2400/04* (2013.01)

(58) Field of Classification Search
CPC .................................................. A61K 38/363
See application file for complete search history.

(56) References Cited

U.S. PATENT DOCUMENTS

| 4,453,939 | A | 6/1984 | Zimmerman et al. |
| 6,056,970 | A * | 5/2000 | Greenawalt ............. A61L 15/32 424/422 |
| 6,762,336 | B1 | 6/2004 | MacPhee et al. |
| 2003/0198659 | A1* | 10/2003 | Hoffmann ............... A01N 25/34 424/411 |
| 2004/0101546 | A1* | 5/2004 | Gorman ................ A61K 31/715 424/445 |
| 2006/0051340 | A1 | 3/2006 | Uchida et al. |
| 2006/0127460 | A1* | 6/2006 | Uchida ............ A61K 47/48976 424/445 |
| 2006/0257458 | A1* | 11/2006 | Gorman ................... A61L 15/26 424/445 |
| 2007/0231372 | A1 | 10/2007 | Imamura et al. |
| 2010/0254961 | A1 | 10/2010 | Nishio et al. |
| 2011/0070288 | A1 | 3/2011 | Andjelic |
| 2012/0095418 | A1 | 4/2012 | Stopek et al. |
| 2015/0125511 | A1* | 5/2015 | Kageyama ............ A61K 38/363 424/443 |

FOREIGN PATENT DOCUMENTS

| EP | 2269594 A1 | 1/2011 |
| JP | 6134830 | 8/1986 |

(Continued)

OTHER PUBLICATIONS

Communication dated May 20, 2015, issued by the European Patent Office in counterpart Application No. 13791531.0.

(Continued)

*Primary Examiner* — Gina C Justice
(74) *Attorney, Agent, or Firm* — Sughrue Mion, PLLC

(57) ABSTRACT

A formed sheet product of a polymer composition comprising at least one protein selected from the group consisting of fibrinogen and thrombin and at least one polymer selected from the group consisting of an aliphatic polyester and a water-soluble polymer, and a laminated formed sheet product comprising a first polymer composition layer composed of fibrinogen and a water-soluble polymer and a second polymer composition layer composed of thrombin and an aliphatic polyester are provided. These formed products are applied onto a wound site and function as a hemostatic material.

19 Claims, 1 Drawing Sheet

(56) References Cited

FOREIGN PATENT DOCUMENTS

| | | |
|---|---|---|
| JP | 2002513645 | 5/2002 |
| JP | 2002515300 | 5/2002 |
| JP | 2005-290610 A | 10/2005 |
| JP | 2008-516735 A | 5/2008 |
| JP | 2009183649 | 8/2009 |
| JP | 2009533135 | 9/2009 |
| JP | 2010-69031 A | 4/2010 |
| JP | 2012-87122 A | 5/2012 |
| WO | 9715188 | 5/1997 |
| WO | 99/25782 A2 | 5/1999 |
| WO | 9956798 | 11/1999 |
| WO | 03/017989 A1 | 3/2003 |
| WO | 2004064878 | 8/2004 |
| WO | 2005113030 | 12/2005 |
| WO | 2006/028244 A1 | 3/2006 |
| WO | 2006/044879 A2 | 4/2006 |
| WO | 2007110783 A2 | 10/2007 |
| WO | 2007117237 | 10/2007 |
| WO | 2009031620 | 3/2009 |
| WO | 2011/037760 A2 | 3/2011 |
| WO | 2011/146360 A1 | 11/2011 |

OTHER PUBLICATIONS

International Preliminary Report on Patentability dated Nov. 18, 2014, with Written Opinion.
Communication dated Apr. 8, 2015 from the Japanese Patent Office in counterpart application No. 2014-515699.
International Search Report of PCT/JP2013/063872, dated Aug. 20, 2013. [PCT/ISA/210].
Communication dated Apr. 12, 2016, from the Singapore Patent Office in counterpart Singapore application No. 11201407549Y.

\* cited by examiner

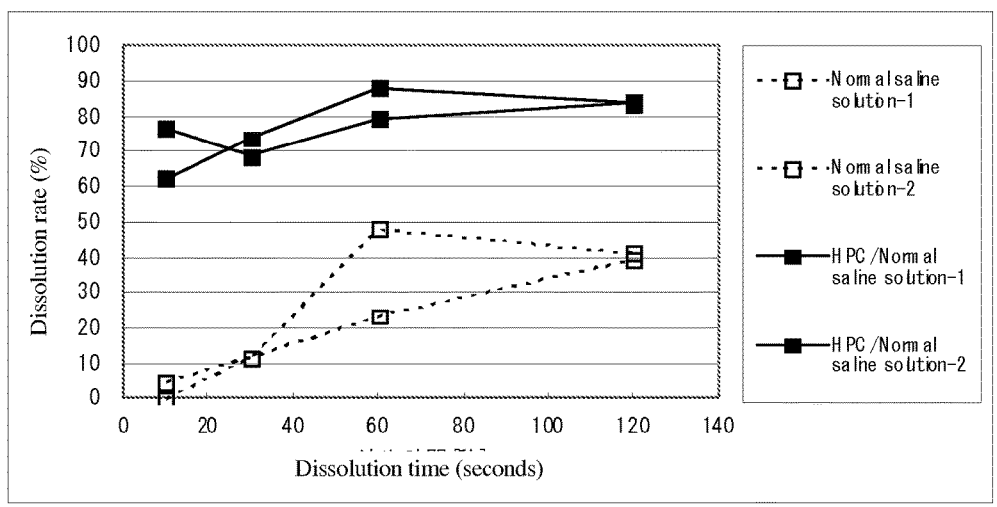

FORMED SHEET PRODUCT AND HEMOSTATIC MATERIAL

CROSS REFERENCE TO RELATED APPLICATIONS

This application is a National Stage of International Application No. PCT/JP2013/063872 filed May 13, 2013, claiming priority based on Japanese Patent Application Nos. 2012-110391, filed May 14, 2012, 2012-110392, filed May 14, 2012, 2012-110393, filed May 14, 2012, 2012-110394, filed May 14, 2012 and 2013-003273, filed Jan. 11, 2013, the contents of all of which are incorporated herein by reference in their entirety.

TECHNICAL FIELD

The present invention relates to a formed sheet product and a hemostatic material comprising the same. More particularly, the present invention relates to a formed sheet product containing fibrinogen and/or thrombin, having good dissolution property and supporting characteristic for these hemostatic proteins, and being excellent in hemostatic property, and a hemostatic material comprising the same.

BACKGROUND ART

Fibrinogen is a blood coagulation factor present in the final stage of the blood coagulation cascade. When a blood vessel is damaged, the coagulation system is activated, and finally, the activated thrombin converts soluble fibrinogen into insoluble fibrin. This fibrin has adhesive strength and exerts important functions in hemostasis and wound healing.

Hemostasis and tissue adhesion operations such as tissue closure hold an important position at the medical site, especially in surgical operations, and fibrin glue adhesives to which this principle is applied are utilized in a wide range of sites of surgical operation.

Various investigations have been conducted and improvements have so far been made on methods for using a fibrin glue adhesive, and examples thereof include liquid preparations for applying or spraying a fibrinogen solution and a thrombin solution to an affected area (two-component preparations: see Japanese Examined Patent Application Publication No. H9-2971 specification and International Publication No. WO97/33633) and a method in which a sheet preparation containing fibrinogen and thrombin in mixture fixed on a support such as collagen is attached to an affected area (see Japanese Unexamined Patent Application Publication No. 2004-521115 specification).

However, in the case of the existing liquid preparations, since lyophilized fibrinogen and thrombin are dissolved separately upon use, it takes several minutes to dissolve a lyophilized preparation, and thus these preparations cannot be said to be satisfactory in terms of responsiveness to emergent surgery and convenience.

In addition, in the case of the above mentioned fibrin glue adhesives, since a higher fibrinogen concentration provides a stronger adhesive strength, a small amount of thrombin at a high concentration must be acted on fibrinogen at a high concentration.

However, in the case of the existing liquid preparations, since equal volumes of a fibrinogen solution and a thrombin solution are mixed upon use, their concentrations are reduced to 50%, preventing fibrinogen to exert its maximum efficacy. Furthermore, since the limit of fibrinogen concentration in a solution is actually about 10%, improvement in terms of concentration is difficult for a system for which two liquids are mixed in an equal volume.

In this respect, since a sheet preparation can apply a fibrinogen solution at a high concentration onto an affected site, stronger adhesive strength can be expected theoretically as compared to a two-component preparation. In addition, the sheet preparation allows astriction/compression closure at a projectile/exudative bleeding site and is expected to have excellent convenience.

When a sheet-like tissue adhesive is used, tissue penetration of the sheet preparation must be increased when applied on a wound site in order to apply a fibrinogen solution at a high concentration to the affected site. Furthermore, since a sheet preparation may be rolled or folded to closely attach to a wound site, flexibility and two-component retaining power of the sheet must be increased to prevent damage of the sheet or dropout of the fibrinogen component and thrombin component due to such force.

Sheet-like tissue adhesives and sheet-like hemostatic materials in which an active ingredient is fixed on various substrates have been disclosed (see Japanese Examined Patent Application Publication No. 61-34830 specification, Japanese Unexamined Patent Application Publication No. 2002-513645 specification, International Publication No. WO2004/064878 and International Publication No. WO2005/113030). Japanese Examined Patent Application Publication No. 61-34830 specification discloses a sheet preparation in which fibrinogen and thrombin are fixed on an equine-derived collagen surface layer and it has been put on a practice ((TachoComb (registered trademark)). However, since the collagen substrate is thick and relatively hard, adhesiveness at a wound site may decrease to make effective closure difficult. This sheet preparation has a support of equine collagen and thus, when it is to be applied to a human subject, there is a risk of development of an antibody against a heterogeneous protein and occurrence of zoonotic infections such as prion disease, and the sheet preparation cannot be said to be ideal.

International Publication of Japanese Unexamined Patent Application Publication No. 2002-513645 specification discloses a paper-like composition in which a hemostatic compound is homogenously distributed. This composition is prepared by forming a fibrous pulp comprising a bioabsorptive polymer and a hemostatic compound (mainly, thrombin, fibrinogen) in a non-aqueous solvent and subjecting the fibrous pulp to papermaking treatment. This composition reduces the time required for hemostasis by a factor of 14 as compared with TachoComb and enables re-attachment. However, since it has a paper-like shape, there is a room for improving tissue-following property.

International Publication No. WO2004/064878 and International Publication No. WO2005/113030 disclose a material using a sheet in which thrombin is fixed on a bioabsorptive synthetic non-woven fabric and a fibrinogen solution in combination. For these compositions, a non-woven fabric is immersed in an aqueous solution of an active ingredient followed by lyophilization to make a composite. This method suffers from problems such as a low yield of the lyophilization step, low flexibility of the sheet, and poor supporting characteristic for fixed protein to lead to peeling-off from the sheet.

Japanese Unexamined Patent Application Publication No. 2009-183649 specification discloses a sheet-like tissue hemostatic material comprising a fibrinogen-containing layer and a thrombin-containing layer provided therebetween with an intermediate layer containing a cellulose derivative as a material; however, there are such problems that the solubility of fibrinogen contained in the tissue hemostatic is insufficient and the handling property is poor and cannot be trimmed since it is a lyophilized product.

In addition, as sheet preparations, Japanese Unexamined Patent Application Publication No. 2010-069031 specification discloses a sheet-like fibrin glue adhesive comprising a bioabsorptive support on which fibrinogen containing a non-ionic surfactant is fixed and a bioabsorptive support on which thrombin is fixed; Japanese Unexamined Patent Application Publication No. 2002-515300 specification discloses a sandwich bandage for hemostasis comprising a fibrinogen layer, a thrombin layer, an absorption material layer and the like; and Japanese Unexamined Patent Application Publication No. 2009-533135 specification discloses a porous wound care product comprising a first absorptive non-woven fabric, and at least one second absorptive woven fabric or knitted fabric, and thrombin and/or fibrinogen. However, since these hemostatic materials are manufactured by lyophilization of fibrinogen and thrombin, fibrinogen and thrombin readily drop off, the material is insufficiently flexible, and the tissue adhesion effect described above is insufficient because fibrinogen and thrombin are present adjacently to each other. In addition, when a preparation is in the form in which fibrinogen and thrombin are in direct contact to each other, coagulation reaction proceeds to form fibrin even with a trace amount of water during storage, causing a problem in storage stability. Further, there was also a problem of requiring vast amounts of time and labor for manufacturing due to the necessity of a lyophilization step.

No sheet-like hemostatic material for which effect and convenience can be expected actually has been established by the combination of fibrinogen and thrombin as described above. Further, although a fibrinogen solution at a high concentration is required to exert a strong tissue adhesion effect, since fibrinogen is poorly soluble, fibrinogen is scarcely dissolved when fibrinogen is fixed on a support while retaining a conventional composition due to poor solubility of fibrinogen and thus sufficient drug efficacy cannot be expected to be exerted.

DISCLOSURE OF THE INVENTION

It is an object of the present invention to provide a formed sheet product which is good in supporting characteristic and dissolution property for hemostatic proteins, that is, fibrinogen and/or thrombin and excellent in flexibility (tissue-following property), eventually hemostasis.

It is another object of the present invention to provide a hemostatic material comprising the formed sheet product according to the present invention as described above which can achieve an excellent hemostatic effect following application onto a wound site.

Further objects and advantages of the present invention will become apparent by the following explanation.

According to the present invention, the objects and advantages of the present invention as described above can be achieved firstly by a formed sheet product of a polymer composition comprising at least one protein selected from the group consisting of fibrinogen and thrombin and at least one polymer selected from the group consisting of an aliphatic polyester and a water-soluble polymer.

According to the present invention, the objects and advantages of the present invention as described above can be achieved secondly by a laminated formed sheet product comprising a first formed sheet product composed of fibrinogen and a water-soluble polymer and a second formed sheet product layer composed of thrombin and an aliphatic polyester as the formed sheet product described in the previous paragraph.

Further, according to the present invention, the objects and advantages of the present invention as described above can be achieved thirdly by a hemostatic material comprising the formed sheet product or laminated formed sheet product described above. In other words, these formed products are applied to a wound site and used as a hemostatic material to treat the wound site.

BRIEF DESCRIPTION OF DRAWING

FIG. 1 shows dissolution of thrombin from a formed fiber product of a polyglycolic acid-polylactic acid copolymer containing thrombin.

PREFERRED EMBODIMENT OF THE INVENTION

The formed sheet product according to the present invention is a formed sheet product of a polymer composition containing at least one protein selected from the group consisting of fibrinogen and thrombin and at least one polymer selected from the group consisting of an aliphatic polyester and a water-soluble polymer (hereinbelow also referred to as "substrate polymer"). The expression "to contain protein" used herein refers the condition where at least part of protein is incorporated into a substrate polymer composition. Such a structure is excellent in protein supporting characteristic, unlike lyophilized composites in which protein is present on the surface of a composition or in gaps of the composition.

The formed sheet product according to the present invention is not limited in particular as far as the product is in a sheet-like form, but preferred examples thereof include a formed fiber product and a formed film product. The formed fiber product is a three-dimensional formed product formed by laminating, weaving, knitting or processing by other techniques a single or plurality of fibers obtained. Specific examples of the formed fiber product include non-woven fabric. In addition, a tube, a mesh and the like prepared therefrom are included in the formed fiber product. The formed film product used herein refers to a film-like formed product prepared by forming methods such as extrusion forming methods such as inflation extrusion and T-dye extrusion, calendaring, and casting.

The formed sheet product according to the present invention can exert its effect when used alone or in combination with a second sheet containing a complementary protein (fibrinogen for thrombin, or thrombin for fibrinogen) in a fibrin glue. When used alone, it is preferably a formed fiber product containing thrombin in an aliphatic polyester.

Further, the formed sheet product described above can be used as a formed sheet product for constituting a laminated formed sheet product with a second formed sheet product according to the present invention, and the laminated formed sheet product with the second formed sheet product according to the present invention is a laminated formed sheet product comprising a first formed sheet product composed of fibrinogen and a water-soluble polymer and a second formed sheet product composed of thrombin and an aliphatic polyester.

Fibrinogen and thrombin used as hemostatic proteins in the present invention may be those prepared from animals and those manufactured by gene recombination technology. As fibrinogen and thrombin derived from animals, those derived from human are preferable. Proteins having a modified amino acid sequence can also be used.

Here, fibrin may be produced partly during storage, especially when the above polymer composition contains fibrinogen and thrombin, and the composition containing such fibrin is included in the range of the present invention.

Pharmaceutically acceptable additives may be added to the hemostatic protein used in the present invention. Examples of such additives include one or more selected from the group consisting of blood coagulation factor XIII, albumin, isoleucine, glycine, arginine, glutamic acid, phenylalanine, histidine, surfactants, sodium chloride, sugar alcohols (glycerol, mannitol, etc.), trehalose, sodium citrate, aprotinin and calcium chloride.

The hemostatic protein or a mixture of the hemostatic protein and the additive(s) may be dispersed as the respective molecules in a substrate polymer, but it is preferable that particles formed by the respective molecules gathered together (hereinbelow the expression "protein particles" may also be used, including mixed particles containing an additive(s)) are dispersed in a substrate polymer. This may improve dissolution of the hemostatic protein and flexibility of the sheet when the formed sheet product is a fiber-like formed product.

In the present invention, the average particle diameter of the protein particles contained is 0.1 to 200 μm. It is technically difficult to prepare particles having a particle diameter smaller than 0.1 μm. Further, when the particle diameter is larger than 200 μm, a formed sheet product becomes fragile and difficult to be handled, which is not preferable. The average particle diameter is preferably 0.5 to 150 μm, and more preferably 1 to 100 μm.

The formed sheet product according to the present invention contains, in the case of a formed fiber product, the protein-containing particles generally in an amount of 1 to 100 mass %, preferably 10 to 100 mass %, more preferably 20 to 100 mass %, and further preferably 50 to 100 mass % based on the substrate polymer. When the content of the protein-containing particles is lower than this value, the dissolution of protein from a formed sheet product and flexibility or hemostatic property of a formed sheet product may become poor; while when the content is higher, the self-support property of a formed sheet product itself decreases, which is not preferable. In addition, in the case of a formed film product, the protein-containing particles are contained generally in an amount of 100 mass % or more, preferably 500 mass % or more, and further more preferably 800 to 950 mass % based on the substrate polymer. When the content is lower than the values, hemostatic property may become poor; and when the content is higher, formability of a film may become poor.

Specific examples of the aliphatic polyester used in the present invention include polylactic acid, polyglycolic acid, a polylactic acid-polyglycolic acid copolymer, polycaprolactone, polyglycerol sebacate, polyhydroxyalkanoic acid, polybutylene succinate, and a derivative thereof. Among these, the aliphatic polyester is preferably selected from the group consisting of polylactic acid, polyglycolic acid, polycaprolactone, and a copolymer thereof, and a mixture thereof.

Here, when a polylactic acid copolymer is used, a monomer component imparting stretching property may be included. Examples of the monomer component imparting stretching property include caprolactone monomer, and a soft component such as ethylene glycol, 1,2-propylene glycol, 1,3-propylene glycol, 1,2-butanediol, 1,4-butanediol, polycaprolactonediol, polyalkylene carbonate diol, polyethylene glycol unit, and the like. Lower amounts of these soft components are preferable and the amount is preferably lower than 50 mol % per polymer unit. When the amount of the soft component is higher than the value, self-support property tend to be lost and the product is too soft to be handled easily.

When a polylactic acid or a copolymer thereof is used, examples of the monomers constituting the polymer may include L-lactic acid and D-lactic acid, but not particularly limited. Although the optical purity, molecular weight, composition ratio of an L-form and a D-form, or sequence of the polymer is not particularly limited, a polymer containing an L-form in a higher quantity is preferable, and a stereo complex of poly L-lactic acid and poly D-lactic acid may also be used. The molecular weight of the polymer is generally $1\times10^3$ to $5\times10^6$, preferably $1\times10^4$ to $1\times10^6$, and more preferably $5\times10^4$ to $5\times10^5$. Furthermore, the terminal structure of the polymer and the catalyst for polymerization to obtain the polymer can be arbitrarily selected.

Preferred examples of the water-soluble polymer used in the present invention include a polymer having an N-vinyl cyclic lactam unit and a water-soluble cellulose derivative.

Examples of the polymer having an N-vinyl cyclic lactam unit include homopolymers or copolymers obtained by polymerizing or copolymerizing N-vinylpyrrolidone and N-vinylcaprolactam. Specific examples of the homopolymer include poly(N-vinyl-2-pyrrolidone), poly(N-vinyl-5-methyl-2-pyrrolidone), poly(N-vinyl-2-piperidone), poly(N-vinyl-6-methyl-2-piperidone), poly(N-vinyl-ϵ-caprolactam), and poly(N-vinyl-7-methyl-ϵ-caprolactam).

Furthermore, specific examples of the copolymer described above include copolymers obtained by copolymerizing N-vinylpyrrolidone, N-vinylcaprolactam or the like with, for example, vinyl acetate, (meth)acrylic acid ester, (meth)acrylic acid, maleic acid ester, maleic acid, acrylonitrile, styrene, alkyl vinyl ether, N-vinylimidazole, vinyl pyridine, allyl alcohol, or olefins. Here, examples of the ester include alkyl esters having 1 to 20 carbon atoms, dimethylaminoalkyl esters and a quaternary salt thereof, and hydroxyalkyl esters. As such a backbone polymer, only one polymer may be used and two or more polymers can be used in combination. Polyvinyl pyrrolidone is the most preferable because of easiness of manufacturing and availability.

The average molecular weight of the polymer having an N-vinyl cyclic lactam unit used in the present invention is not particularly limited, but it is generally $1\times10^3$ to $5\times10^6$, preferably $1\times10^4$ to $1\times10^6$, and more preferably $5\times10^4$ to $5\times10^5$. Furthermore, the terminal structure of the polymer and the catalyst for polymerization to obtain the polymer can be arbitrarily selected.

Moreover, the water-soluble cellulose derivative is selected from the group consisting of hydroxypropyl cellulose, methyl cellulose, hydroxyethyl cellulose, hydroxypropylmethyl cellulose, carboxymethyl cellulose sodium, and a mixture thereof.

Among these, the water-soluble cellulose derivative is preferably selected from the group consisting of hydroxypropyl cellulose, hydroxyethyl cellulose, hydroxypropylmethyl cellulose, and a mixture thereof and is most preferably hydroxypropyl cellulose.

The molecular weight of the water-soluble cellulose derivative used in the present invention is not particularly limited, and for example, the viscosity measured at a concentration of 2% and at 20° C. is generally 1 to 10000 mPa·s, preferably 2 to 5000 mPa·s, and more preferably 2 to 4000 mPa·s.

In the formed sheet product according to the present invention, other polymers and other compounds can be used in combination as far as they do not impair the object of the present invention. For example, copolymers, polymer blends, or compound mixtures may be conducted. Examples of the compound to be incorporated include phospholipids and surfactants.

The polymer used in the present invention is preferably of high purity, and especially the amounts of residual matters such as additives, a plasticizer, a remaining catalyst, remaining monomers, and residual solvents used in the forming processing and post-processing are preferably as low as possible. Especially when used in the medical practice, the content must be controlled to a level lower than the safety standards.

The average thickness of the formed sheet product according to the present invention is, for a formed fiber product, generally 10 to 1000 μm, preferably 50 to 200 μm, and more preferably 100 to 150 μm. When the thickness is smaller than the values, a formed sheet product cannot retain its strength so that trimming cannot be performed, which is not preferable; while when the thickness is larger than these values, flexibility and/or hemostatic property of a formed sheet product decreases, which is not preferable. When the formed sheet product is a formed film product, its average thickness is generally 5 to 200 μm, and preferably 10 to 100 μm.

When the formed sheet product according to the present invention contains fibrinogen, fibrinogen is preferably contained at content in the range of 0.05 to 30 $mg/cm^2$. When the content of fibrinogen is lower than 0.05 $mg/cm^2$, the effect based on the protein property is not exhibited; while when the content is higher than 30 $mg/cm^2$, the formed fiber product itself becomes fragile, which is not preferable. The content is preferably 0.1 to 25 $mg/cm^2$, and more preferably 0.2 to 25 $mg/cm^2$. Furthermore, especially when the formed sheet product is a formed film product, the fibrinogen content is 2 $mg/cm^2$ or less, preferably 1.5 $mg/cm^2$ or less, and more preferably 1.4 $mg/cm^2$ or less from the viewpoint of hemostasis.

When the formed sheet product according to the present invention contains thrombin, the content of thrombin is preferably in the range of 0.1 to 100 $U/cm^2$. When the content of thrombin is lower than 0.1 $U/cm^2$, the hemostatic effect is not exhibited; and when the content is higher than 100 $U/cm^2$, the formed sheet product itself becomes fragile, which is not preferable. The content is preferably 2 to 80 $U/cm^2$, and more preferably 5 to 50 $U/cm^2$.

The formed fiber product in the present invention refers to a three-dimensional formed product formed by laminating, weaving, knitting or processing by other techniques a single or plurality of fibers obtained. Specific examples of the formed fiber product include non-woven fabric. In addition, a tube, mesh, and the like prepared therefrom are included in the formed fiber product.

When the formed sheet product according to the present invention is a formed fiber product, a preferable average fiber diameter is 0.01 to 50 μm. When the average fiber diameter is smaller than 0.01 μm, a formed fiber product cannot retain strength, which is not preferable. Further, when the average fiber diameter is larger than 50 μm, since the specific area of the fiber decreases and thus the solubility of hemostatic protein becomes poor, which is not preferable. More preferably, the average fiber diameter is 0.02 to 30 μm. Here, a fiber diameter refers to a diameter of a cross section of a fiber. The shape of a cross section of a fiber is not limited to round and may be elliptic or irregular. In this case, the fiber diameter is calculated as an average of the length of the ellipse in the direction of the major axis and the length in the direction of the minor axis. When the cross section of a fiber is neither round nor ellipse, a fiber diameter is calculated by approximating to a round or ellipse.

When the formed sheet product according to the present invention is a formed fiber product, the fabric weight per unit area (hereinafter termed as METSUKE) thereof is preferably 0.1 to 50 $mg/cm^2$. When the METSUKE is smaller than 0.1 $mg/cm^2$, the hemostatic protein cannot be sufficiently supported, which is not preferable. Further, when the METSUKE is larger than 50 $mg/cm^2$, the possibility of inducing inflammation increases, which is not preferable. The METSUKE is more preferably 0.2 to 20 $mg/cm^2$.

When the formed sheet product according to the present invention is a formed fiber product, the bulk density thereof is preferably 100 to 200 $mg/cm^3$. When the bulk density is lower than 100 $mg/cm^3$, handling property is deteriorated, which is not preferable. Further, when the bulk density is higher than 200 $mg/cm^3$, void in the formed fiber product decreases and the flexibility and the dissolution of the hemostatic protein are reduced, which is not preferable.

When the formed sheet product according to the present invention is a formed fiber product, the manufacturing method is not particularly limited and any method adopted for manufacturing plastic fiber can be adopted; however, it is preferable to be performed by solution forming so that the hemostatic protein or hemostatic protein-containing particles are easily dispersed in order to prevent a decrease in the activity of the hemostatic protein. In addition, the formed fiber product is preferably in the form of filament. The filament specifically refers to a formed fiber product that is formed, without subjecting to a step of cutting fibers, during the process from spinning to processing to a formed fiber product, and can be formed by electrospinning, spun bonding, melt blowing, and the like, but electrospinning is preferably used.

The electrospinning is a method in which a polymer is dissolved in a solvent and a high voltage is applied to the solution to obtain a formed fiber product on the electrode. The method includes a step of dissolving a polymer in a solvent to prepare a solution, a step of applying a high voltage to the solution, a step of ejecting the solution, and a step of evaporating the solvent from the ejected solution to form a formed fiber product, and optional step of eliminating the electric charge of the formed fiber product and a step of accumulating the formed fiber product by eliminating the electric charge.

The step of producing a spinning dope in the electrospinning is explained. As the spinning dope in the present invention, a suspension composed of a substrate polymer solution and hemostatic protein particles is preferably used.

The concentration of the substrate polymer in the suspension is preferably 1 to 30 mass %. When the polymer concentration is lower than 1 mass %, it is difficult to form a formed fiber product, which is not preferable. Further, when the concentration is higher than 30 mass %, the fiber diameter of the obtained formed fiber product attained becomes larger and the viscosity of the suspension increases, which is not preferable. A more preferable concentration of the polymer in the suspension is 1.5 to 20 mass %.

The solvent for the water-soluble polymer is not particularly limited as far as the solvent can dissolve the water-soluble polymer and form a suspension with hemostatic protein particles, evaporate during the step of spinning, and form a fiber, and one solvent may be used or a plurality of solvents may be used in combination. Examples of the solvent include chloroform, 2-propanol, toluene, benzene, benzyl alcohol, dichloromethane, carbon tetrachloride, cyclohexane, cyclohexanone, trichloroethane, methyl ethyl ketone, ethyl acetate, acetone, ethanol, methanol, tetrahydrofuran, 1,4-dioxane, 1-propanol, phenol, pyridine, acetic acid, formic acid, hexafluoro-2-propanol, hexafluoroacetone, N,N-dimethylformamide, N,N-dimethylacetamide, acetonitrile, N-methyl-2-pyrrolidinone, N-methylmorpholine-N-oxide, 1,3-dioxolane, water, and mixed solvents of these solvents. Among these, dichloromethane, chloroform, 2-propanol, ethanol, and N,N-dimethylformamide are preferably used in terms of handling property, physical properties, and the like.

The solvents for dissolving an aliphatic polyester are not particularly limited as far as the solvent can dissolve the aliphatic polyester and form a suspension with hemostatic protein particles, evaporate during the step of spinning, and form a fiber, and one solvent may be used or a plurality of solvents may be used in combination. Examples of the solvent include chloroform, 2-propanol, toluene, benzene, benzyl alcohol, dichloromethane, carbon tetrachloride, cyclohexane, cyclohexanone, trichloroethane, methyl ethyl ketone, ethyl acetate, and mixed solvents thereof. Further, solvents such as acetone, ethanol, methanol, tetrahydrofuran, 1,4-dioxane, 1-propanol, phenol, pyridine, acetic acid, formic acid, hexafluoro-2-propanol, hexafluoroacetone, N,N-dimethylformamide, N,N-dimethylacetamide, acetonitrile, N-methyl-2-pyrrolidinone, N-methylmorpholine-N-oxide, 1,3-dioxolane may be contained as far as an emulsion can be formed. Among these, dichloromethane and ethanol are preferably used in terms of handling property and physical properties.

The method of preparing such a suspension is not particularly limited and ultrasonic and various stirring methods can be used. As the stirring method, high-speed stirring using such as a homogenizer and stirring methods using an attritor, a ball mill, or the like can be used. Among these, a dispersing method using ultrasonic treatment is preferable.

Further, a spinning dope can be prepared by forming a suspension with a solvent and hemostatic protein particles and then adding a water-soluble polymer or aliphatic polyester.

In addition, prior to preparation of a suspension, hemostatic protein particles can be subjected to a refining treatment. The refining treatment includes dry grinding and wet grinding, and both methods can be adopted and both can be used in combination in the present invention. The dry grinding treatment includes treatment using a ball mill, treatment using a planetary mill or a vibrational mill, treatment of grinding in a mortar with a pestle, a media stirring type pulverizer, an impact pulverizer such as a hammer mill, a jet mill, and grinding treatment using a grindstone. The wet grinding treatment includes treatment in which hemostatic protein dispersed in an appropriate dispersion medium is stirred using a stirring device having a high shearing force, a kneader, or the like, treatment of a dispersion in a medium by a ball mill, and bead mill treatment. Further, hemostatic protein particles prepared using a spray drier can also be used.

The step of applying a high voltage to the solution, the step of ejecting the solution, and the step of evaporating the solvent from the ejected solution to form a formed fiber product are then described.

In the method of manufacturing a formed fiber product according to the present invention, a high voltage must be applied to a suspension in order to eject a suspension composed of a polymer solution and hemostatic protein particles to form a formed fiber product. The method for applying a voltage is not particularly limited as far as the method can eject a suspension to form a formed fiber product; however, the method includes a method in which an electrode is immersed in a solution to apply a voltage, and a method in which a voltage is applied to a solution ejection nozzle.

In addition, an auxiliary electrode can be provided in addition to an electrode that applies voltage on a solution. The value of voltage to be applied is not particularly limited as far as the formed fiber product can be formed, but generally it is preferably in the range of 5 to 50 kV. When the applied voltage is lower than 5 kV, a spinning dope is not ejected so that a formed fiber product is not formed, which is not preferable; and when the applied voltage is higher than 50 kV, electric discharge from the electrode to the earth electrode occurs, which is not preferable. More preferably, the voltage is in the range of 10 to 30 kV. A desired potential may be created by any appropriate method.

Accordingly, immediately after the suspension composed of a polymer solution and hemostatic protein particles is ejected, a solvent evaporates to form a formed fiber product. Spinning is generally conducted under atmospheric pressure at room temperature, but it can be conducted under a negative pressure when evaporation is insufficient or in the atmosphere at a high temperature. Further, the spinning temperature depends on the evaporation behavior of the solvent and the viscosity of the spinning liquid, but it is generally in the range of 0 to 50° C.

Then, the step in which the the formed fiber product is processed to eliminate its electric charge and made to accumulate will be described below. The method for eliminating the electric charge of a formed fiber product and for accumulating the fiber product is not particularly limited, but examples thereof include a method in which a formed fiber product is collected on an earth electrode to eliminate the electric charge and made to accumulate simultaneously. A method in which electric charge is eliminated prior to accumulation using an ionizer, and the like is also included. In this case, the method for accumulating the formed fiber product is not particularly limited, but general methods thereof include a method in which electrostatic force is made to disappear by the electric charge elimination, wherein the formed fiber product falls down by its own weight and is subsequently made to accumulate. Further, as required, a method in which a formed fiber product from which the electrostatic force is lost is sucked and accumulated on a mesh, a method in which air is convected in an apparatus to accumulate the product on a mesh, or the like may implemented. The ionizer used herein refers to an apparatus in which ions are generated by a built-in ion generator and the ions are discharged onto a charged matter to cause the electric charge of the charged matter to disappear. Examples of preferable ion generator constituting the ionizer used in the method for manufacturing a formed fiber product according to the present invention include an apparatus that generates ions by applying a high voltage to a built-in discharge needle.

Such electrospinning methods are known, and the apparatus or conditions are not limited as far as the formed fiber product according to the present invention can be prepared. However, in addition to Examples below, the description of, for example, International Publication No. WO2004/072336 specification and International Publication No. 2005/087988 specification can be referred.

When the formed sheet product according to the present invention is a formed film product, any method conventionally adopted as a method for manufacturing a film may be used as a method for manufacturing the product. Examples of the method include casting. Such forming can be conducted by melt forming as well as solution forming; however, in order to prevent a decrease in activity of the hemostatic protein, solution forming is preferable so that the hemostatic protein is easily dispersed.

Next, the laminated formed sheet product according to the present invention will be explained.

The laminated formed sheet product according to the present invention comprises a first polymer composition layer containing fibrinogen and a water-soluble polymer and a second polymer composition layer containing thrombin and an aliphatic polyester.

The water-soluble polymer is selected from among a cellulose derivative, polymer having an N-vinyl cyclic lactam unit, polyethylene oxide, polyvinyl alcohol, hyaluronic acid, dextran, Pullulan or starch, or a mixture thereof.

The water-soluble polymer is preferably a cellulose derivative or a polymer having an N-vinyl cyclic lactam unit, or a mixture thereof is preferable.

Specific examples of the cellulose derivative are those selected from the group consisting of hydroxypropyl cellulose, methyl cellulose, hydroxyethyl cellulose, hydroxypropylmethyl cellulose, and carboxymethyl cellulose sodium, and a mixture thereof.

Among these, the cellulose derivative is preferably selected from the group consisting of hydroxypropyl cellulose, hydroxyethyl cellulose, hydroxypropylmethyl cellulose, polyvinylpyrrolidone, and a mixture thereof, and most preferably hydroxypropyl cellulose or polyvinylpyrrolidone.

Further, the average molecular weight of the polymer having an N-vinyl cyclic lactam unit as the water-soluble polymer is not particularly limited, but is $1\times10^3$ to $5\times10^6$, preferably $1\times10^4$ to $1\times10^6$, and more preferably $5\times10^4$ to $5\times10^5$. In addition, the terminal structure of the polymer and the catalyst for polymerization of the polymer can be arbitrarily selected.

The viscosity of the cellulose derivative as the water-soluble polymer, measured at a concentration of 2% and at 20° C., is preferably 0.01 to 10000 mPa·s, more preferably 0.1 to 5000 mPa·s, further more preferably 0.1 to 1000 mPa·s, and most preferably 0.1 to mPa·s.

Other polymers and other compounds can be used in combination with the water-soluble polymer as far as they do not impair the object of the present invention. For example, co-polymers, polymer blends, or a compound mixture may be cited.

Such a water-soluble polymer is preferably of highl purity, and especially, the amounts of a plasticizer contained in the polymer, a residual catalyst, a residual monomer, and residual substances such as residual solvents used for forming processing and post-processing are preferably lower. Especially, when the product is used in medical practice, the amounts of residual substances must be controlled to a level lower than the safety standards.

Further, the layer composed of a water-soluble polymer and fibrinogen may further contain pharmaceutically acceptable additives. Examples of such additives may include those described above in the explanation for the formed sheet product. Especially when fibrinogen is particles having an average particle diameter of 0.01 to 100 μm, these additives are preferably added in the particles.

As the aliphatic polyester, those described above in the explanation of the formed sheet product can similarly be used.

Other polymers and other compounds can be used in combination with the aliphatic polyester as far as they do not impair the object of the present invention. For example, co-polymers, polymer blends, or a compound mixture may be cited.

Such an aliphatic polyester is preferably of high purity, and especially, the amounts of additives contained in the polymer, a residual catalyst, a residual monomer, and residual substances such as residual solvents used for forming processing and post-processing are preferably lower. Especially, when the product is used in medical practice, the amounts of residual substances must be controlled to a level lower than the safety standards.

Further, the layer composed of an aliphatic polyester and thrombin may further contain pharmaceutically acceptable additives. Examples of such additives may be one or more selected from the group consisting of polyhydric alcohols, surfactants, amino acids, oligosaccharides, sodium chloride, sodium citrate, and calcium chloride. This may result in improvement in stability and solubility of thrombin, flexibility, and the like.

The first polymer composition layer composed of a water-soluble polymer and fibrinogen preferably is composed of a formed fiber product or a film. The formed fiber product used herein refers to a three-dimensional formed product prepared by laminating, weaving, knitting or processing by other techniques a single or plurality of fibers obtained. Specific examples of the formed fiber product include non-woven fabric. In addition, a tube, a mesh and the like prepared therefrom are included in the formed fiber product.

The film can be manufactured by any conventionally adopted method. An example of the method is casting. Such forming can be conducted by melt forming as well as solution forming; however, in order to prevent a decrease in activity of the hemostatic protein, solution forming is preferable so that the hemostatic protein is easily dispersed.

The average fiber diameter of the formed fiber product composed of a water-soluble polymer and fibrinogen is 0.01 to 50 μm. When the average fiber diameter is smaller than 0.01 μm, a formed fiber product cannot retain strength, which is not preferable. Further, when the average fiber diameter is larger than 50 μm, since the specific area of the fiber decreases and thus the solubility of hemostatic protein becomes poor, which is not preferable. More preferably, the average fiber diameter is 0.02 to 30 μm. Here, a fiber diameter refers to a diameter of a cross section of a fiber. The shape of a cross section of a fiber is not limited to round and may be elliptic or irregular. In this case, the fiber diameter is calculated as an average of the length of the ellipse in the direction of the major axis and the length in the direction of the minor axis. When the cross section of a fiber is neither round nor ellipse, a fiber diameter is calculated by approximating to a round or ellipse.

The average thickness of the laminated formed sheet product according to the present invention is preferably 50 to 350 μm, more preferably 100 to 300 μm, and further more preferably 100 to 250 μm.

The METSUKE of the formed fiber product composed of a water-soluble polymer and fibrinogen is preferably 0.1 to 50 mg/cm$^2$. When the METSUKE is smaller than 0.1 mg/cm$^2$, fibrinogen cannot be sufficiently supported, which is not preferable. Also, when the METSUKE is larger than 50 mg/cm$^2$, the possibility of causing inflammation becomes high, which is not preferable.

The bulk density of the formed fiber product composed of a water-soluble polymer and fibrinogen is preferably 100 to 200 mg/cm$^3$. When the bulk density is lower than 100 mg/cm$^3$, handling property is deteriorated, which is not preferable. Further, when the bulk density is higher than 200 mg/cm$^3$, void in the formed fiber product decreases to lower the flexibility and the dissolution of the hemostatic protein, which is not preferable.

The formed fiber product composed of a water-soluble polymer and fibrinogen generally contains fibrinogen at the content in the range of 0.05 to 30 mg/cm$^2$. When the content of fibrinogen is lower than 0.05 mg/cm$^2$, the hemostatic effect is not exhibited, and when the content is larger than 30 mg/cm$^2$, the formed fiber product itself becomes fragile, which is not preferable. The content is preferably 0.1 to 25 mg/cm$^2$, and more preferably 0.2 to 25 mg/cm$^2$. In addition, especially when the formed sheet product is a formed film product, from the viewpoint of hemostasis, the fibrinogen content is 2 mg/cm$^2$ or less, preferably 1.5 mg/cm$^2$ or less, and more preferably 1.4 mg/cm$^2$ or less.

The formed fiber product composed of a water-soluble polymer and fibrinogen is preferably in the form of filament. The filament specifically refers to a formed fiber product that is formed, without subjecting to a step of cutting fibers, during the process from spinning to processing to a formed fiber product, and can be formed by electrospinning, spun bonding, melt blowing, and the like, but electrospinning is preferably used.

With electrospinning, the diameter of the fibrinogen powder is preferably in the range of 0.01 to 100 μm, when a suspension is prepared by mixing a water-soluble polymer and fibrinogen powder described in the explanation of the formed sheet product above. It is technically difficult to prepare particles having a particle diameter smaller than 0.01 μm, and when the particle diameter is larger than 100 μm, dispersibility is poor, and a formed fiber product becomes fragile and difficult to be handled, which is not preferable.

The film composed of a water-soluble polymer and fibrinogen can be produced by any method that has been adopted conventionally. An example thereof is casting. Such forming can be conducted by melt forming as well as solution forming; however, in order to prevent a decrease in activity of the hemostatic protein, solution forming is preferable so that the hemostatic protein is easily dispersed.

The content of the water-soluble polymer of the film composed of a water-soluble polymer and fibrinogen is preferably 0.1 to 50 mass %, and more preferably 0.5 to mass %, although it depends on the type of polymer. In addition, the protein-containing particles of fibrinogen are contained generally in an amount of 100 mass % or more, preferably 500 mass % or more, and further more preferably 800 to 950 mass % based on the water-soluble polymer. When the content is lower than the values, hemostatic property may become poor; and when the content is higher, formability of a film may become poor.

The average thickness of the film composed of a water-soluble polymer and fibrinogen is preferably 10 to 1000 μm.

The film composed of a water-soluble polymer and fibrinogen preferably contains fibrinogen at the content in the range of 0.05 to 10 mg/cm$^2$. When the content of fibrinogen is lower than 0.05 mg/cm$^2$, the hemostatic effect is not exhibited, and when the content is larger than 10 mg/cm$^2$, the film itself becomes fragile, which is not preferable. The content is more preferably 0.1 to 8 mg/cm$^2$, and more preferably 0.2 to 4 mg/cm$^2$.

In the present invention, the second polymer composition layer composed of an aliphatic polyester and thrombin preferably is composed of a formed fiber product. The definition of the formed fiber product is described above.

The average fiber diameter of the formed fiber product composed of an aliphatic polyester and thrombin is 0.01 to 50 μm. When the average fiber diameter is smaller than 0.01 μm, the formed fiber product cannot retain strength, which is not preferable. In addition, when the average fiber diameter is larger than 50 μm, since the specific surface area of the fiber becomes small and thus the release of thrombin is deteriorated, which is not preferable. More preferably, the average fiber diameter is 0.02 to 30 μm.

The average thickness of the formed fiber product composed of an aliphatic polyester and thrombin is 10 to 1000 μm. When the average thickness is smaller than 10 μm, the formed fiber product cannot retain its strength so that trimming cannot be performed, which is not preferable. In addition, when the thickness is larger than 1000 μm, flexibility and/or hemostatic property of the formed sheet product decreases, which is not preferable. The average thickness is more preferably 20 to 500 μm.

The METSUKE of the formed fiber product composed of an aliphatic polyester and thrombin is 0.1 to 50 mg/cm$^2$. When the METSUKE is smaller than 0.1 mg/cm$^2$, thrombin cannot be sufficiently supported, which is not preferable. Also when the METSUKE is larger than 50 mg/cm$^2$, the possibility of causing inflammation becomes high, which is not preferable. The METSUKE is more preferably 0.2 to 20 mg/cm$^2$.

The bulk density of a formed fiber product composed of an aliphatic polyester and thrombin is 100 to 200 mg/cm$^3$. When the bulk density is lower than 100 mg/cm$^3$, handling property decreases, which is not preferable. Also, when the bulk density is higher than 200 mg/cm$^3$, void in the formed fiber product decreases to lower the flexibility and the release of the hemostatic protein, which is not preferable.

In the present invention, the formed fiber product composed of an aliphatic polyester and thrombin preferably contains thrombin at the content of 0.1 to 100 U/cm$^2$. When the content of thrombin is lower than 0.1 U/cm$^2$, the hemostatic effect is insufficient, which is not preferable. When the content is higher than 100 U/cm$^2$, the formed fiber product itself becomes fragile, which is not preferable. The content is preferably 2 to 80 U/cm$^2$, and more preferably 5 to 50 U/cm$^2$. The protein-containing particles of thrombin generally in an amount of 1 to 200 mass %, preferably 10 to 100 mass %, more preferably 20 to 100 mass %, and further preferably 50 to 100 mass % based on the aliphatic polyester. When the content of the protein-containing particles is lower than this value, the dissolution of thrombin from a formed sheet product and flexibility or hemostatic property of a formed sheet product may become poor; while when the content is higher, the self-support property of a formed sheet product itself decreases, which is not preferable.

The formed fiber product composed of an aliphatic polyester and thrombin preferably is in the form of filament. The meaning and manufacturing method of the filament are as described above.

Such a formed fiber product composed of an aliphatic polyester and thrombin can be manufactured by the electrospinning method. The electrospinning method is as described for the formed sheet product above. When an aliphatic polyester and thrombin powder are mixed to prepare a suspension, the diameter of the thrombin powder is not particularly limited, but preferably in the range of 0.01 to 100 μm. It is technically difficult to prepare thrombin powder having a diameter smaller than 0.01 µm, and when the diameter of the thrombin powder is larger than 100 µm, dispersibility is poor and the formed fiber product becomes fragile, which is not preferable.

Processings such as further laminating a cotton-like fiber structure on the surface of the formed sheet product according to the present invention or on the surface of each layer of the laminated formed sheet product, and placing a cotton-like structure between layers of the laminated formed sheet product according to the present invention to provide a sandwich structure can be performed arbitrarily as far as they do not impair the object of the present invention.

A drug can be optionally contained inside the fibers of the formed fiber product of the formed sheet product and the laminated formed sheet product according to the present invention. When electrospinning is used for forming, any drug can be used without particular limitation as far as the drug is soluble in an organic solvent or aqueous solution and does not lose its physiological activities by dissolution.

The laminated formed sheet product according to the present invention is composed of one or more first polymer composition layer composed of a water-soluble polymer and fibrinogen and one or more second polymer composition layer composed of an aliphatic polyester and thrombin; however, layers other than these can be further provided. The order laminating these layers is not limited, and similar layers may be adjacent to each other in some parts.

In the laminated formed sheet product according to the present invention, the first polymer composition layer composed of a water-soluble polymer and fibrinogen and the second polymer composition layer composed of an aliphatic polyester and thrombin may be layered to each other, and a layer can be further laminated by a general coating method on either of the formed layer. Methods such as electrospinning, electrospraying, casting, immersion, ejection, pressing, and thermal pressing may be performed. Especially, as a method for laminating a layer composed of a formed fiber product on a layer composed of a formed fiber product, the electrospinning method is preferred. The formed fiber product composed of an aliphatic polyester and thrombin formed fiber may be laminated on the formed fiber product composed of a water-soluble polymer and fibrinogen, or the formed fiber product composed of a water-soluble polymer and fibrinogen is laminated on the formed fiber product composed of an aliphatic polyester and thrombin.

When the laminated formed sheet product according to the present invention is applied to a wound site as a hemostatic material, it is preferable that the layer composed of a water-soluble polymer and fibrinogen is in contact with the wound site. This allows the layer composed of a water-soluble polymer and fibrinogen to start to dissolve as soon as the layer composed of a water-soluble polymer and fibrinogen is made into contact with the wound site so that fibrinogen penetrates the wound site sufficiently, and then thrombin is immediately released from the layer composed of an aliphatic polyester and thrombin so that coagulation reaction accompanying fibrin production proceeds. Here, after the aliphatic polyester in the layer composed of the aliphatic polyester and thrombin functions as a reinforcement element required for astriction, the polyester is decomposed over time.

The formed sheet product and laminated formed sheet product according to the present invention are thin and excellent in flexibility, and thus provide good adhesive property to a wound site. In addition, since the formed sheet product and laminated formed sheet product according to the present invention contain active ingredients, fibrinogen and/or thrombin in the formed fiber product and the like, supporting characteristic is excellent unlike lyophilized products. At the same time, since the solubility of fibrinogen and release and dissolution to the fibrinogen layer of thrombin are superior, hemostatic effect appears in a short time. Since the hemostatic effect appears in a short time, the required amount of fibrinogen is small, thus the product is excellent also in cost. The formed sheet product according to the present invention is excellent in visibility of a wound site after being applied to the wound site by selection of its material to be used. Due to this, since it is possible to confirm hemostatic state visibly, though it has been difficult so far, it is possible to determine a site to be sutured easily in case suture is needed.

Further, since no lyophilization step is required for manufacturing the formed sheet product and laminated formed sheet product according to the present invention, productivity is excellent.

EXAMPLES

The embodiments of the present invention will be explained referring to Examples below, but the Examples will not limit the scope of the present invention.
<Measurement Methods for Examples 1 to 6 and 16 to 29 and Comparative Examples 1 and 2>
1A. Particle Diameter of Protein Particles (Average Particle Diameter):

Lyophilized fibrinogen powder ground in a mortar was photographed at a magnification of 1000 times using a digital microscope (KEYENCE Corporation: trade name "VHX-100"), 10 particles were selected randomly from the photo and measured for a diameter, and the average obtained was used as an average particle diameter.

2A. Average Fiber Diameter:

The surface of the formed fiber product obtained was photographed at a magnification of 3000 times using a scanning electron microscope (KEYENCE Corporation: trade name "VE8800"), and 20 sites were selected randomly from the photo, from which the diameter of the fiber was measured for all the fibers, and the average obtained was used as an average mean fiber diameter. n=20.

3A. Average Thickness:

A film thickness of a formed fiber product obtained (n=15) was measured using a high-accuracy digital measuring instrument (Mitutoyo Corporation: trade name "Litematic VL-50") at the measuring power of 0.01 N and the average film thickness was calculated. In this measurement, the minimum possible measuring power for the instrument was used.

4A. METSUKE:

A formed fiber product obtained was cut into a piece of 50 mm×100 mm and weighed, and the weight was converted into METSUKE.

5A. Bulk Density

A bulk density was calculated from the value of METSUKE measured as described above and the average thickness.

6A. Dissolution Test:

A formed fiber product obtained was cut into a piece of 1 cm×1 cm, and 15 µL of normal saline solution was added to the piece to confirm its solubility.

7A. ELISA Assay
(1) Fibrinogen

To an ELISA plate (N UNC 468667), anti-human fibrinogen antibody (DAKO A0080) was fixed at 10 µg/mL. After washing with PBS containing 0.05% Tween 20, Block Ace (DS Pharma Biomedical Co., Ltd., UK-B80) was added to each well for masking. After washing with PBS containing 0.05% Tween 20, a specimen was added. Human fibrinogen (Enzyme Research Laboratories No. FIB3) was used as a standard substance to prepare a calibration curve. After washing with PBS containing 0.05% Tween 20, HRP-labeled anti-human fibrinogen antibody (CPL5523) was added, and the mixture was reacted, and then the reaction mixture was washed with PBS containing 0.05% Tween 20. Subsequently, TMB reagent (KPL 50-76-02 50-65-02) was added, and the mixture was allowed to stand for 6 minutes for color development. 1 M $H_3PO_4$ was added to stop color development and OD was measured for a range between 450 and 650 nm by a microplate reader.

(2) Thrombin

To an ELISA plate (N UNC 468667), anti-human thrombin antibody (Affinity Biologicals Inc., No. SAHT-AP) was fixed at 5 μg/mL. After washing with PBS containing 0.05% Tween 20, Block Ace (DS Pharma Biomedical Co., Ltd. UK-B80) was added to each well for masking. After washing with PBS containing 0.05% Tween 20, a specimen is added. Human thrombin (Haematologic Technologies, Inc.: HCT-0020) was used as a standard substance to prepare a calibration curve. After washing with PBS containing 0.05% Tween 20, HRP-labeled anti-human thrombin antibody (Affinity Biologicals Inc., No. SAHT-HRP) was added at 0.1 μg/mL. After the reaction, the mixture was washed with PBS containing 0.05% Tween 20, TMB reagent (DAKo S1599) was added, and the mixture was allowed to stand for 10 minutes for color development. 0.5 M $H_2SO_4$ was added to stop color development, and OD was measured in a range between 450 and 650 nm by a microplate reader.

8A. Measurement of Thrombin Activity

To a 2008 tube of Falcon, 20 μL of a sample, 60 μL of a buffer containing 50 mM Tris-HCl (pH 8.5)+50 mM NaCl, and 20 μL of 0.1% PLURONIC F-68 were added, and the mixture was incubated at 37° C. for 3 minutes. As standard substances, human-plasma derived purified α-thrombin (purchased from Haematologic Technologies, Inc.: HCT-0020) diluted with the same buffer to 5, 2.5, 1.25, 0.625, and 0.3125 U/mL were used. To each of the reaction solutions, 100 μL of Testzym chromogenic substrate S-2238 (1 mM: Daiichi Kagaku Yakuhin Kogyo) was added, and the mixture was stirred and mixed to react at 37° C. for 5 minutes, and then 800 μL of a 0.1 M citric acid solution was added to quench the reaction. 200 μL of the reaction solution was transferred to a 96-well plate and OD was measured in a range between 405 and 650 nm.

Example 1

Lyophilized fibrinogen powder (BOLHEAL (registered trademark, the same applied below) for tissue adhesive: vial 1) was ground in a mortar to prepare ground lyophilized fibrinogen powder having an average particle diameter of 14 μm. After this ground lyophilized fibrinogen powder was dispersed in ethanol, polyvinylpyrrolidone (K90, Wako Pure Chemical Industries, Ltd.) was dissolved to make 10 mass % to prepare a spinning dope of lyophilized fibrinogen powder/polyvinylpyrrolidone=100/100 (w/w). Spinning was conducted at a temperature of 22° C. and a humidity of 26% or lower by an electrospinning method to obtain a sheet-like formed fiber product. The inner diameter of the ejection nozzle was 0.8 mm, the voltage was 13.5 kV, the flow rate of the spinning dope was 1.2 mL/h, and the distance between the ejection nozzle and the plate was 15 cm. The average fiber diameter of the formed fiber product obtained was 0.51 μm, the average thickness was 285 μm, the METSUKE was 2.35 mg/cm², and the bulk density was 82 mg/cm³. The formed fiber product obtained was subjected to a dissolution test and it was dissolved within 1 second. Further, the sheet obtained was cut into 0.5 cm×0.5 cm, protein was extracted using 62.5 μL of normal saline solution, and ELISA assay was conducted. The results show that the amount of the fixed protein was 0.54 mg/cm². The sheet obtained could be trimmed with scissors.

Example 2

After the lyophilized fibrinogen powder ground in Example 1 was dispersed in ethanol, polyvinylpyrrolidone (K90, Wako Pure Chemical Industries, Ltd.) was dissolved to make 10 mass % to prepare a spinning dope of lyophilized fibrinogen powder/polyvinylpyrrolidone=100/200 (w/w). Spinning was conducted at a temperature of 22° C. and a humidity of 26% or lower by an electrospinning method to obtain a sheet-like formed fiber product. The inner diameter of the ejection nozzle was 0.8 mm, the voltage was 17 kV, the flow rate of the spinning dope was 1.2 mL/h, and the distance between the ejection nozzle and the plate was 15 cm. The average fiber diameter of the formed fiber product obtained was 0.33 μm, the average thickness was 469 μm, the METSUKE was 5.28 mg/cm², and the bulk density was 113 mg/cm³. The formed fiber product obtained was subjected to a dissolution test and it was dissolved within 1 second. Further, the sheet obtained was cut into 0.5 cm×0.5 cm, protein was extracted using 62.5 μL of normal saline solution, and ELISA assay was conducted. The results show that the amount of the fixed protein was 1.61 mg/cm². The sheet obtained could be trimmed with scissors.

Example 3

After the lyophilized fibrinogen powder ground in Example 1 was dispersed in 2-propanol, hydroxypropyl cellulose (6 to 10 mPa·s, Wako Pure Chemical Industries, Ltd.) was dissolved to make 16 mass % to prepare a spinning dope of lyophilized fibrinogen powder/hydroxypropyl cellulose=20/100 (w/w). Spinning was conducted at a temperature of 22° C. and a humidity of 26% or lower by an electrospinning method to obtain a sheet-like formed fiber product. The inner diameter of the ejection nozzle was 0.8 mm, the voltage was 11 kV, the flow rate of the spinning dope was 1.2 mL/h, and the distance between the ejection nozzle and the plate was 15 cm. The average fiber diameter of the formed fiber product obtained was 0.86 μm, the average thickness was 137 μm, the METSUKE was 1.59 mg/cm², and the bulk density was 116 mg/cm³. The formed fiber product obtained was subjected to a dissolution test and it was dissolved within 1 second. Further, the sheet obtained was cut into 0.5 cm×0.5 cm, protein was extracted using 62.5 μL of normal saline solution, and ELISA assay was conducted. The results show that the amount of the fixed protein was 0.17 mg/cm². The sheet obtained could be trimmed with scissors.

Comparative Example 1

The lyophilized fibrinogen powder ground in Example 1 was dissolved in 1,1,1,3,3,3-hexafluoro-2-propanol/MINIMUM ESSENTIAL MEDIUM EAGLE (Sigma-Aldrich Co. LLC.) 10×(9/1=v/v) to make 15 w/v %. Spinning was conducted at a temperature of 22° C. and a humidity of 26% or lower by an electro spinning method to obtain a sheet-like formed fiber product. The inner diameter of the ejection nozzle was 0.8 mm, the voltage was 23.5 kV, the flow rate of the spinning liquid was 2.45 mL/h, and the distance between the ejection nozzle and the plate was 12 cm. The formed fiber product obtained was subjected to a dissolution test and it was not dissolved.

Comparative Example 2

After lyophilized fibrinogen powder was dissolved in a solution for dissolving fibrinogen (both were contained in BOLHEAL for tissue adhesive), hydroxypropyl cellulose (6 to 10 mPa·s, Wako Pure Chemical Industries, Ltd.) was dissolved to make 16 mass % to prepare a spinning dope of lyophilized fibrinogen powder/hydroxypropyl cellulose=20/100 (w/w); however, phase separation occurred between hydroxypropyl cellulose and fibrinogen occurred and fibrinogen was deposited so that electrospinning could not be conducted.

Example 4

After the lyophilized fibrinogen powder ground in Example 1 was dispersed in 2-propanol, hydroxypropyl cellulose (6 to 10 mPa·s, Wako Pure Chemical Industries, Ltd.) was dissolved to make 16 mass % to prepare a spinning dope of lyophilized fibrinogen powder/hydroxypropyl cellulose=40/100 (w/w). Spinning was conducted at a temperature of 22° C. and a humidity of 26% or lower by an electrospinning method to obtain a sheet-like formed fiber product. The inner diameter of the ejection nozzle was 0.8 mm, the voltage was 12.5 kV, the flow rate of the spinning dope was 1.2 mL/h, and the distance between the ejection nozzle and the plate was 15 cm. The mean fiber diameter of the formed fiber product obtained was 0.43 μm, the average thickness was 152 μm, the METSUKE was 1.86 mg/cm$^2$, and the bulk density was 122 mg/cm$^3$. The formed fiber product obtained was subjected to a dissolution test and it was dissolved within 1 second. Further, the sheet obtained was cut into 0.5 cm×0.5 cm, protein was extracted using 62.5 μL of normal saline solution, and ELISA assay was conducted. The results show that the amount of the fixed protein was 0.30 mg/cm$^2$. The sheet obtained could be trimmed with scissors.

Example 5

After the lyophilized fibrinogen powder ground in Example 1 was dispersed in 2-propanol, hydroxypropyl cellulose (6 to 10 mPa·s, Wako Pure Chemical Industries, Ltd.) was dissolved to make 16 mass % to prepare a spinning dope of lyophilized fibrinogen powder/hydroxypropyl cellulose=100/100 (w/w). Spinning was conducted at a temperature of 22° C. and a humidity of 26% or lower by an electrospinning method to obtain a sheet-like formed fiber product. The inner diameter of the ejection nozzle was 0.8 mm, the voltage was 12.5 kV, the flow rate of the spinning dope was 1.2 mL/h, and the distance between the ejection nozzle and the plate was 15 cm. The average fiber diameter of the formed fiber product obtained was 0.35 μm, the average thickness was 191 μm, the METSUKE was 2.74 mg/cm$^2$, and the bulk density was 143 mg/cm$^3$. The formed fiber product obtained was subjected to a dissolution test and it was dissolved within 1 second. Further, the obtained sheet was cut into 0.5 cm×0.5 cm, protein was extracted using 62.5 μL of normal saline solution, and activity measurement and ELISA assay were conducted. The results show that the amount of the fixed protein was 0.51 mg/cm$^2$. The sheet obtained could be trimmed with scissors.

Example 6

<Preparation of a Layer Composed of an Aliphatic Polyester and Thrombin>

After lyophilized thrombin powder (BOLHEAL for tissue adhesive: vial 3) ground in a mortar as in Example 1 was dispersed in ethanol, dichloromethane was added, and polylactic acid (PL18, Purac Biomaterials) was dissolved to make 10 mass % to prepare a spinning dope of lyophilized thrombin powder/polylactic acid=100/100 (w/w). Spinning was conducted at a temperature of 22° C. and a humidity of 26% or lower by an electrospinning method to obtain a sheet-like formed fiber product. The inner diameter of the ejection nozzle was 0.8 mm, the voltage was 15 kV, the flow rate of the spinning dope was 3.0 mL/h, and the distance between the ejection nozzle and the plate was 25 cm. The obtained sheet was cut into 2 cm×2 cm, and protein was extracted using 1 mL of normal saline solution and activity measurement and ELISA assay were conducted. The results show that the measured activity value was 23 U/cm$^2$ and the value measured by ELISA was 16 μg/cm$^2$.

<Evaluation Test for Tissue Adhesion Effect>

In order to confirm the activity of fibrinogen, an adhesion test was conducted on a combination of the layer composed of a water-soluble polymer and fibrinogen prepared in Example 5 and the layer composed of an aliphatic polyester and thrombin prepared in Example 6. For the adhesive strength, the skin of a rabbit was adhered on the sheet (2 cm×2 cm) and it was examined whether or not a fibrin gel was formed and adhered. In this procedure, 200 μL of water was added to the layer composed of a water-soluble polymer and fibrinogen in advance and the layer composed of a water-soluble polymer and fibrinogen was attached to the skin of a rabbit after 40 seconds of the wetting. After that, the skin and the sheet were allowed to stand at 37° C. for 3 minutes and then adhesion between the skin and the sheet was examined. As a control, a collagen sheet preparation on which the component of a fibrin adhesive was fixed (trade name: TachoComb/CSL Behring Co., Ltd.): components such as fibrinogen and thrombin are firmly fixed on one side of a sponge-like equine collagen sheet as a support by vacuum drying: 2 cm×2 cm) was used. The results show that the sheet subjected to evaluation had adhesive strength equal to or higher than that of the collagen sheet preparation used as the control for comparison.

<Discussion>

The use of 1,1,1,3,3,3-hexafluoro-2-propanol/MINIMUM ESSENTIAL MEDIUM EAGLE 10×(9/1=v/v) in Comparative Example 1 was to allow manufacturing of a formed fiber product from a lyophilized fibrinogen powder by an electro spinning method. Since fibrinogen is difficult to be dissolved in an aqueous solvent, this lyophilized fibrinogen powder contains an additive for increasing the solubility of fibrinogen. Although this lyophilized fibrinogen powder was used as it was, fibrinogen was not dissolved from the formed fiber product prepared from this lyophilized fibrinogen powder in Comparative Example 1.

On the contrary, in Examples 1 to 5, fibrinogen was made into particles having an average particle diameter of 0.01 to 100 μm, and a dispersion of the particles was prepared. When the dispersion was contained in a polymer soluble in water and ethanol, dissolution within 1 second could be achieved. In addition, from Example 6, it is shown that the physiological activities of the hemostatic protein are retained in the formed sheet product according to the present invention.

On the other hand, in Comparative Example 2, referring to International Publication No. WO2009/031620, an attempt was made to dissolve lyophilized fibrinogen powder of BOLHEAL as it was in a solution for dissolving fibrinogen and to mix the resultant solution with a water-soluble cellulose derivative solution; however, a homogenous composition could not be obtained.

<Measurement Methods for Examples 7 to 13>

1B. Dispersibility of Fibrinogen, Thrombin, and Fibrin in a Spinning Dope:

Dispersions of fibrinogen, thrombin, and fibrin immediately before the addition of an aliphatic polyester were observed visually to confirm dispersibility of these proteins.

2B. Thickness of Formed Fiber Product:

It was measured by the same method as that in 1A.

3B. Fiber Diameter (Average Fiber Diameter):

It was measured by the same method as that in 2A.

4B. Handling Property of Sheet:

Whether or not a formed fiber product obtained could be easily handled was evaluated qualitatively.

Example 7

Lyophilized fibrinogen powder (BOLHEAL for tissue adhesive: vial 1) was ground into particulates using a jet mill (SWISHING ENTERPRISE Co., Ltd.: trade name "AO Jet Mill"). The particulates were added to ethanol (Wako Pure Chemical Industries, Ltd.) and the mixture was treated by an ultrasonic bath for 5 minutes to prepare a fibrinogen dispersion having excellent dispersibility. A homogeneous solution was prepared by adding dichloromethane (Wako Pure Chemical Industries, Ltd.) and polylactic acid in the L-form at 100% (Purser PL18, Purac) to the dispersion obtained to dissolve polylactic acid. The polylactic acid solution obtained for spinning was prepared to have a polylactic acid concentration of 10 mass %, a lyophilized fibrinogen powder concentration of 4 mass % (1.8 mass % as fibrinogen), and a ratio of ethanol to dichloromethane of 1:8 by weight. The protein/organic solvent dispersion before the addition of polylactic acid was observed visually and it was found that the dispersion was in a homogenous dispersed state with no precipitation. Spinning of the polylactic acid solution obtained was conducted at a humidity of 30% or lower by an electrospinning method to obtain a sheet-like formed fiber product. The inner diameter of the ejection nozzle was 0.8 mm, the voltage was 12 kV, and the distance between the ejection nozzle and the plate was 25 cm. The plate described above was used as an anode in spinning. The formed fiber product obtained had an average fiber diameter of 3.3 μm and a thickness of 161 μm, was flexible, and could be handled. Here, when dichloromethane was used in place of ethanol above (in Example 14), the handling property of the formed fiber product obtained decreased, and from this point of view, ethanol was considered more preferable.

Example 8

Lyophilized thrombin powder (BOLHEAL for tissue adhesive: vial 3) was added to ethanol (Wako Pure Chemical Industries, Ltd.) and the mixture was treated by an ultrasonic bath for 5 minutes to prepare a thrombin dispersion having excellent dispersibility. A homogeneous solution was prepared by adding dichloromethane (Wako Pure Chemical Industries, Ltd.) and polylactic acid in the L-form at 100% (Purasorb PL18, Purac) to the dispersion obtained to dissolve polylactic acid. The polylactic acid solution obtained for spinning was prepared to have a polylactic acid concentration of 10 mass %, a lyophilized thrombin powder concentration of 4 mass % (0.045 mass % as thrombin), and a ratio of ethanol to dichloromethane of 1:8 by weight. The protein/organic solvent dispersion before the addition of polylactic acid was observed visually and it was found that the dispersion was in a homogenous dispersed state with no precipitation. Spinning of the polylactic acid solution obtained was conducted at a humidity of 30% or lower by an electrospinning method to obtain a sheet-like formed fiber product. The inner diameter of the ejection nozzle was 0.8 mm, the voltage was 12 kV, and the distance between the ejection nozzle and the plate was 25 cm. The plate described above was used as an anode in spinning. The formed fiber product obtained had an average fiber diameter of 6.2 μm and a thickness of 170 μm, was flexible, and could be handled. Here, when dichloromethane was used in place of ethanol above in (Example 15), the handling property of the obtained formed fiber product decreased, and from this point of view, ethanol was considered more preferable.

Example 9

Lyophilized thrombin powder (BOLHEAL for tissue adhesive: vial 3) was added to ethanol (Wako Pure Chemical Industries, Ltd.) and the mixture was treated by an ultrasonic bath for 5 minutes to prepare a thrombin dispersion having excellent dispersibility. A homogenous solution was prepared by adding dichloromethane (Wako Pure Chemical Industries, Ltd.) and polylactic acid in the L-form at 100% (Purasorb PL18, Purac) to the dispersion obtained to dissolve polylactic acid. The polylactic acid solution obtained for spinning was prepared to have a polylactic acid concentration of 10 mass %, a lyophilized thrombin powder concentration of 7 mass % (0.078 mass % as thrombin), and a ratio of ethanol to dichloromethane of 1:8 by weight. The protein/organic solvent dispersion before the addition of polylactic acid was observed visually and it was found that the dispersion was in a homogenous dispersed state with no precipitation. Spinning of the polylactic acid solution obtained was conducted at a humidity of 30% or lower by an electrospinning method to obtain a sheet-like formed fiber product. The inner diameter of the ejection nozzle was 0.8 mm, the voltage was 12 kV, and the distance between the ejection nozzle and the plate was 25 cm. The plate described above was used as an anode in spinning. The formed fiber product obtained had an average fiber diameter of 8.1 μm and a thickness of 175 μm, was flexible, and could be handled.

Example 10

Lyophilized thrombin powder (BOLHEAL for tissue adhesive: vial 3) was added to ethanol (Wako Pure Chemical Industries, Ltd.) and the mixture was treated by an ultrasonic bath for 5 minutes to prepare a thrombin dispersion having excellent dispersibility. A homogenous solution was prepared by adding dichloromethane (Wako Pure Chemical Industries, Ltd.) and polylactic acid in the L-form at 100% (Purasorb PL18, Purac) to the dispersion obtained to dissolve polylactic acid. The polylactic acid solution obtained for spinning was prepared to have a polylactic acid concentration of 10 mass %, a lyophilized thrombin powder concentration of 10 mass % (0.11 mass % as thrombin), and a ratio of ethanol to dichloromethane of 1:8 by weight. The protein/organic solvent dispersion before the addition of polylactic acid was observed visually and it was found that the dispersion was in a homogenous dispersed state with no precipitation. Spinning of the polylactic acid solution obtained was conducted at a humidity of 30% or lower by an electrospinning method to obtain a sheet-like formed fiber product. The inner diameter of the ejection nozzle was 0.8 mm, the voltage was 12 kV, and the distance between the ejection nozzle and the plate was 25 cm. The plate described above was used as an anode in spinning. The formed fiber product obtained had an average fiber diameter of 9.4 µm and a thickness of 210 µm, was flexible, and could be handled.

Example 11

Lyophilized thrombin powder (BOLHEAL for tissue adhesive: vial 3) was added to ethanol (Wako Pure Chemical Industries, Ltd.) and the mixture was treated by an ultrasonic bath for 5 minutes to prepare a thrombin dispersion having excellent dispersibility. A homogenous solution was prepared by adding dichloromethane (Wako Pure Chemical Industries, Ltd.) and a polyglycolic acid-polylactic acid copolymer (Purasorb PL5010, Purac) to the dispersion obtained to dissolve the polyglycolic acid-polylactic acid copolymer. The polyglycolic acid-polylactic acid copolymer solution obtained for spinning was prepared to have a polymer concentration of 10 mass %, a lyophilized thrombin powder concentration of 5 mass % (0.06 mass % as thrombin), and a ratio of ethanol to dichloromethane of 1:8 by weight. The protein/organic solvent dispersion before the addition of the polyglycolic acid-polylactic acid copolymer was observed visually and it was found that the dispersion was in a homogenous dispersed state with no precipitation. Spinning of the polyglycolic acid-polylactic acid copolymer solution obtained was conducted at a humidity of 30% or lower by an electrospinning method to obtain a sheet-like formed fiber product. The inner diameter of the ejection nozzle was 0.8 mm, the voltage was 15 kV, and the distance between the ejection nozzle and the plate was 25 cm. The plate described above was used as an anode in spinning. The formed fiber product obtained had an average fiber diameter of 4.8 µm and a thickness of 330 µm, was flexible, and could be handled.

Example 12

Lyophilized thrombin powder (BOLHEAL for tissue adhesive: vial 3) was added to 2-propanol (Wako Pure Chemical Industries, Ltd.) and the mixture was treated by an ultrasonic bath for 5 minutes to prepare a thrombin dispersion having excellent dispersibility. A homogenous solution was prepared by adding dichloromethane (Wako Pure Chemical Industries, Ltd.) and a polyglycolic acid-polylactic acid copolymer (Purasorb PL5010, Purac) to the dispersion obtained to dissolve the polyglycolic acid-polylactic acid copolymer. The polyglycolic acid-polylactic acid copolymer solution obtained for spinning was prepared to have a polymer concentration of 10 mass %, a lyophilized thrombin powder concentration of 5 mass % (0.06 mass % as thrombin), and a ratio of 2-propanol to dichloromethane of 1:8 by weight. The protein/organic solvent dispersion before the addition of the polyglycolic acid-polylactic acid copolymer was observed visually and it was found that the dispersion was in a homogenous dispersed state with no precipitation. Spinning of the polyglycolic acid-polylactic acid copolymer solution obtained was conducted at a humidity of 30% or lower by an electrospinning method to obtain a sheet-like formed fiber product. The inner diameter of the ejection nozzle was 0.8 mm, the voltage was 15 kV, and the distance between the ejection nozzle and the plate was 25 cm. The plate described above was used as an anode in spinning. The formed fiber product obtained had an average fiber diameter of 6.4 µm and a thickness of 320 µm, was flexible, and could be handled.

Example 13

After lyophilized thrombin powder (prepared by lyophilization of recombinant thrombin 1 mg/mL, 3.4% sodium chloride, 1.2% sodium citrate, 0.29% calcium chloride, 1% mannitol at pH 7) was dispersed in ethanol, dichloromethane was added to the dispersion, and a polyglycolic acid-polylactic acid copolymer (Purasorb PDLG5010, Purac) was dissolved to make 10 mass % to prepare a spinning dope of lyophilized thrombin powder/polyglycolic acid-polylactic acid copolymer=100 (1.67 as thrombin)/100 (w/w). Spinning was conducted at temperature of 26° C. and a humidity of 29% or lower by an electrospinning method to obtain a sheet-like formed fiber product. The inner diameter of the ejection nozzle was 0.8 mm, the voltage was 20V, the flow rate of the spinning dope was 4.0 mL/h, and the distance between the ejection nozzles to the earthed plate was 35 cm. The formed fiber product obtained had a thickness of 136 µm, was flexible, and could be handled. Dissolution of thrombin from the sheet obtained was examined by the dissolution test. The test method is as shown below.

<Dissolution Test>
(1) A sample was punched out to have a diameter of 6 mm and its mass was measured.
(2) The sample was placed in a microtube and a dissolution test was conducted in a HPC-containing normal saline solution or normal saline solution.
(3) The sampling times are 10, 30, 60, and 120 seconds.
(4) The sample that had been sampled was subjected to measurement by liquid chromatography and a thrombin content was obtained from a peak area.
(5) The dissolution rate was obtained using the following equation:

$$\text{Dissolution rate (\%)} = \text{The content of thrombin obtained/theoretical content of the fixed thrombin} \times 100$$

The theoretical content of the fixed thrombin was calculated based on a charged thrombin amount (mass %) and a METSUKE of the formed fiber product.

The results of the dissolution test are shown in FIG. 1. The dissolution rate was improved with the HPC-containing normal saline solution than with normal saline solution. This shows that incorporation of HPC in a sheet contributes to improvement of the dissolution rate of thrombin in the laminated formed sheet product according to the present invention.

<Measurement Methods for Examples 14 to 15 and Comparative Examples 3 to 4>
1C. Particle Diameter of Hemostatic Protein Particles (Average Particle Diameter):
A spinning dope was photographed at a magnification of 1000 times using a digital microscope (KEYENCE Corporation: trade name "VHX-100"), 10 particles were randomly selected from the photo and measured for a diameter. The average was used as an average particle diameter.

2C. Thickness of the Formed Fiber Product:

It was measured by the same method as that in 1A.

3C. Fiber Diameter (Average Fiber Diameter):

It was measured by the same method as that in 2A.

4C. Dissolution Test of Hemostatic Protein:

A formed fiber product obtained was cut into a piece of 2 cm×2 cm, and the piece was immersed in 1 mL of normal saline solution for 3 minutes or 3 hours to dissolve a water-soluble component. A change in the weight between before and after the immersion (n=3 to 6) and an average extraction rate was calculated by the following equation. A theoretical weight of the water-soluble component was calculated based on a charged hemostatic protein (mass %) and a METSUKE of a formed fiber product. Extraction rate [%]=(decrease in weight [mg]/theoretical weight [mg] of a water-soluble component)×100

5C. Test for Supporting Characteristic for Hemostatic Protein:

A formed fiber product obtained was cut into a piece of 1 cm×1 cm and the piece was divided into 4 pieces with scissors. The weight was measured before and after the division, and a change in weight was calculated.

Change in weight [%]=(Weight after division [mg]/weight before division [mg])×100

6C. Flexibility Test of Formed Fiber Product:

Referring to (JIS-L-1906 8.19.2 B method) slide method, the size of a test specimen was set as 0.5 cm×3.5 cm and flexibility was measured by the following procedure. After the body of the test apparatus was aligned with the upper surface of a movable platform, a test specimen was placed with 0.5 cm in width sandwiched between a cover glass and the body of the test apparatus. The movable platform was lowered, and a lowered length δ value at which the free end of the test specimen separated from the movable platform was calculated (larger δ values indicate higher flexibility).

Example 14

Lyophilized fibrinogen powder (BOLHEAL for tissue adhesive: vial 1) was ground into particulates using a jet mill (SEISHIN ENTERPRISE Co., Ltd.: trade name "AO Jet Mill"). The particulates were added to dichloromethane (Wako Pure Chemical Industries, Ltd.) and the mixture was treated by an ultrasonic bath for 5 minutes to prepare a fibrinogen dispersion having excellent dispersibility. A solution was prepared by adding polylactic acid in the L-form at 100% (Purasorb PL18, Purac) to dissolve the polymer. The polymer solution obtained for spinning was prepared to have a polymer concentration of 10 mass % and a lyophilized fibrinogen powder concentration of 4 mass % (1.8 mass % as fibrinogen). The particle diameter of fibrinogen dispersed in the spinning dope was 12 µm. Spinning of the polymer solution obtained was conducted at humidity of 30% or lower by an electrospinning method to obtain a sheet-like formed fiber product. The inner diameter of the ejection nozzle was 0.8 mm, the voltage was 12 kV, and the distance between the ejection nozzle and the plate was 25 cm. The plate described above was used as an anode in spinning. The formed fiber product obtained had an average fiber diameter of 14.9 µm and a thickness of 325 µm. The amount of fibrinogen contained in the sheet, which was calculated from the sheet weight and charge ratio, was 0.43 mg/cm². The extraction rate after immersion for 3 hours was 40%. No change in the weight was observed in the supporting characteristic test (100% retention). The δ value obtained from the flexibility test was 2.7 cm.

Example 15

Lyophilized thrombin powder (BOLHEAL vial 3) (containing 1.12% thrombin (750 units) in 40 mg of lyophilized powder) was added to dichloromethane (Wako Pure Chemical Industries, Ltd.) and the mixture was treated by an ultrasonic bath for 5 minutes to prepare a thrombin dispersion. A solution was prepared by adding polylactic acid in the L-form at 100% (Purasorb PL18, Purac) to dissolve the polymer. The polymer solution obtained for spinning was prepared to have a polymer concentration of 10 mass % and a lyophilized thrombin powder concentration of 4 mass % (0.045 mass % or 750 units (U)/g as thrombin). The particle diameter of thrombin dispersed in the spinning dope was 9 µm. Spinning of the polymer solution obtained was conducted at humidity of 30% or lower by an electrospinning method to obtain a sheet-like formed fiber product. The inner diameter of the ejection nozzle was 0.8 mm, the voltage was 12 kV, and the distance between the ejection nozzle and the plate was 25 cm. The plate described above was used as an anode in spinning. The formed fiber product obtained had an average fiber diameter of 16.6 µm and a thickness of 291 µm. The amount of thrombin contained in the sheet, which was calculated from the sheet weight and charge ratio, was 31.39 U/cm².

Comparative Example 3

Lyophilized thrombin powder (BOLHEAL for tissue adhesive: vial 3) was added to ethanol (Wako Pure Chemical Industries, Ltd.), and the mixture was treated by an ultrasonic bath for 5 minutes to prepare a thrombin dispersion. A homogenous solution was prepared by adding dichloromethane (Wako Pure Chemical Industries, Ltd.) and polylactic acid in the L-form at 100% (Purasorb PL18, Purac) to the dispersion obtained to dissolve the polymer. The polymer solution obtained for spinning was prepared to have a polymer concentration of 10 mass %, a lyophilized thrombin powder concentration of 4 mass % (0.045 mass % or 750 U/g as thrombin), a ratio of ethanol to dichloromethane of 1:8 by weight. The particle diameter of thrombin dispersed in the spinning dope was 12 µm. The polymer solution was dried in air to make a solid state. It was subjected to the dissolution test as for the formed fiber product, and as a result, about 3% of the water-soluble component was extracted after immersion for 3 minutes.

Comparative Example 4

NEOVEIL (registered trademark, Gunze Limited), a polyglycolic acid-based non-woven fabric, was used as a formed fiber product to prepare a fibrinogen-fixed sheet by the following procedure (lyophilization method). The above formed fiber product (5×5 cm²) was impregnated with 1.25 mL of a fibrinogen solution contained in the commercially available biotissue adhesive (trade name: BOLHEAL: KAKETSUKEN (the Chemo-Sero-Therapeutic Research Institute)) kit. This specimen was frozen, and then lyophilized for 24 hours, and the resultant was used as a fibrinogen-fixed sheet. In the supporting characteristic test, fibrinogen supported was decomposed to become powder and lost (a change in weight of 89%). The δ value obtained from the flexibility test was 0.7 cm.

<Measurement Methods for Example 16 to 29>
1D. Particle Diameter of Protein Powder (Average Particle Diameter)

Lyophilized fibrinogen powder was ground by a mortar and subjected to particle size distribution measurement using a laser diffraction particle size distribution measurement apparatus (Malvern: trade name "Master Sizer 2000") and the D50 value (median diameter) was determined as an average particle diameter.

2D. Measurement of Fibrinogen Content

The sheet obtained was cut into Φ 0.5 cm, and then fibrinogen was extracted with a 0.1% TFA solution and quantified by high performance liquid chromatography.

<Test Conditions>

Detector: UV absorption spectrophotometer (measurement wave length: 214 nm)
Column: Agilent Bio SEC-3 (3 µm, 30 nm, 4.6×300 mm, Agilent Technologies)
Column temperature: 35° C.
Sampler temperature: 5° C.
Mobile phase: Water containing 0.1% TFA/acetonitrile containing 0.1% TFA=50/50
Flow rate: 0.5 mL/min
Analytical duration: 10 min Example 16

<Preparation of a Formed Sheet Product Composed of a Water-Soluble Polymer and Fibrinogen>

After lyophilized fibrinogen powder (BOLHEAL for tissue adhesive: vial 1) was dispersed in 2-propanol, hydroxypropyl cellulose (6 to 10 mPa·s, Wako Pure Chemical Industries, Ltd.) was dissolved to make 16 mass % to prepare a spinning dope of lyophilized fibrinogen powder/hydroxypropyl cellulose=100 (46 as fibrinogen)/100 (w/w). Spinning was conducted at a temperature of 22° C. and a humidity of 26% or lower by an electrospinning method to obtain a sheet-like formed fiber product. The inner diameter of the ejection nozzle was 0.8 mm, the voltage was 12.5 kV, the flow rate of the spinning dope was 1.2 mL/h, and the distance between the ejection nozzle and the earthed plate was 15 cm. The average fiber diameter of the formed fiber product obtained was a 0.35 µm, the average thickness was 191 µm, the METSUKE was 2.74 mg/cm$^2$, and the bulk density was 143 mg/cm$^3$. The sheet obtained was cut into a piece of 0.5 cm×0.5 cm, protein was extracted using 62.5 µL of normal saline solution, and subjected to ELISA assay (method described in "7A. ELISA assay (1) fibrinogen"). The results show that the amount of the fixed protein was 0.51 mg/cm$^2$.

Example 17

<Preparation of a Formed Sheet Product Composed of an Aliphatic Polyester and Thrombin>

After lyophilized thrombin powder (BOLHEAL for tissue adhesive: vial 3) was dispersed in ethanol, dichloromethane was added to dispersion, and polylactic acid (PL18 Purac Biomaterials) was dissolved to make 10 mass % to prepare a spinning dope of lyophilized thrombin powder/polylactic acid=100 (1.1 as thrombin)/100 (w/w). Spinning was conducted at a temperature of 22° C. and a humidity of 26% or lower by an electrospinning method to obtain a sheet-like formed fiber product. The inner diameter of the ejection nozzle was 0.8 mm, the voltage was 15 kV, the flow rate of the spinning dope was 3.0 mL/h, and the distance between the ejection nozzle and the earthed plate was 25 cm. The average fiber diameter of the formed fiber product obtained was 9.37 µm, the average thickness was 210 µm, the METSUKE was 3.15 mg/cm$^2$, and the bulk density was 150 mg/cm$^3$. The sheet obtained was cut into 2 cm×2 cm, protein was extracted using 1 mL of normal saline solution and subjected to the activity measurement (the method described in "8A. Measurement of thrombin activity") and ELISA assays (the method described in "7A. ELISA assay (2) thrombin"). The results show that the measured activity value was 23.0 U/cm$^2$ and the value measured by ELISA was 16 µg/cm$^2$.

Example 18

<Test for Evaluating Tissue Adhesion Effect of Laminated Formed Sheet Product>

In order to confirm the effect obtained when the formed sheet product composed of a water-soluble polymer and fibrinogen prepared in Example 16 and the formed sheet product composed of an aliphatic polyester and thrombin prepared in Example 17 were used in combination, a comparison of adhesive strength was conducted. For the adhesive strength, the skin of a rabbit was adhered on the sheet (2 cm×2 cm) and it was examined whether or not a fibrin gel was formed and adhered. In this procedure, 200 µL of water was added to the formed sheet product composed of a water-soluble polymer and fibrinogen in advance and the formed sheet product composed of a water-soluble polymer and fibrinogen was attached to the skin of a rabbit after 40 seconds of the wetting. After that, the skin and the sheet were allowed to stand at 37° C. for 3 minutes and then adhesion between the skin and the sheet was evaluated. As a control, a collagen sheet preparation on which the component of a fibrin adhesive was fixed (trade name: TachoComb/CSL Behring Co., Ltd.: components such as fibrinogen and thrombin firmly fixed on one side of a sponge-like equine collagen sheet as a support by vacuum drying: 2 cm×2 cm) was used. The results show that the laminated formed sheet product according to the present invention had adhesive strength equal to or higher than that of the collagen sheet preparation used as the control for comparison.

Example 19

<Preparation of a Formed Sheet Product Composed of a Water-Soluble Polymer and Fibrinogen>

After lyophilized fibrinogen powder (BOLHEAL for tissue adhesive: vial 1) was dispersed in 2-propanol, and hydroxypropyl cellulose (6 to 10 mPA·S Wako Pure Chemical Industries, Ltd.) was dissolved in the dispersion to make 16 mass % to prepare a spinning dope of lyophilized fibrinogen powder/hydroxypropyl cellulose=100 (46 as fibrinogen)/100 (w/w). Spinning was conducted at a temperature of 22° C. and a humidity of 26% or lower by an electrospinning method to obtain a sheet-like formed fiber product. The inner diameter of the ejection nozzle was 0.8 mm, the voltage was 12.5 kV, the flow rate of the spinning dope was 1.2 mL/h, and the distance between the ejection nozzle and the earthed plate was 15 cm. The average fiber diameter of the formed fiber product obtained was 0.35 µm, the average thickness was 191 µm, the METSUKE was 2.74 mg/cm$^2$, and the bulk density was 143 mg/cm$^3$. The sheet obtained was sterilized by electron beam at 20 kGy. The sterilized sheet was cut into 0.5 cm×0.5 cm, and protein was extracted using 62.5 µL of normal saline solution and subjected to ELISA assay (the method described in "7A.

ELISA assay (1) fibrinogen"). The results show that the amount of the fixed protein was 0.78 mg/cm².

Example 20

<Preparation of Formed Sheet Product Composed of an Aliphatic Polyester and Thrombin>

After lyophilized thrombin powder (BOLHEAL for tissue adhesive: vial 3) was dispersed in ethanol, dichloromethane was added to the dispersion, and polylactic acid (PL18 Purac Biomaterials) was dissolved to make 10 mass % to prepare a spinning dope of lyophilized thrombin powder/polylactic acid=100 (1.1 as thrombin)/100 (w/w). Spinning was conducted at a temperature of 22° C. and a humidity of 26% or lower by an electrospinning method to obtain a sheet-like formed fiber product. The inner diameter of the ejection nozzle was 0.8 mm, the voltage was 15 kV, the flow rate of the spinning dope was 3.0 mL/h, and the distance between the ejection nozzle and the earthed plate was 25 cm. The average fiber diameter of the formed fiber product obtained was 9.37 µm, the average thickness was 210 µm, the METSUKE was 3.15 mg/cm², and the bulk density was 150 mg/cm³. The formed sheet product obtained was sterilized by electron beam at 20 kGy. The formed sheet product obtained was cut into 2 cm×2 cm, protein was extracted using 1 mL of normal saline solution and subjected to activity measurement (the method described in "8A. Measurement of thrombin activity") and ELISA assay (the method described in "7A. ELISA assay (2) thrombin"). The results show that the measured activity value was 14.7 U/cm² and the value measured by ELISA was 11.4 µg/cm².

Example 21

<Hemostatic Effect on Exudative Bleeding in Rabbit Liver>

The hemostatic effect obtained when the formed sheet product composed of a water-soluble polymer and fibrinogen prepared in Example 19 and the formed sheet product composed of an aliphatic polyester and thrombin prepared in Example 20 were used in combination was compared with the hemostatic effect obtained when TachoComb was used.

Rabbits were used as an animal hemostasis model. A rabbit was laparotomized to remove a part of the liver, and a formed sheet product composed of a water-soluble polymer and fibrinogen and a formed sheet product composed of an aliphatic polyester and thrombin were applied in an overlapping manner on the bleeding site and the hemostatic effect (presence/absence of hemostasis, amount of bleeding) was observed. The test method is as shown below.
(1) Selactar at 10 mg/kg (about 1.0 mL) and Ketalar at 50 mg/kg (about 3.0 mL) were administered intramuscularly.
(2) The body weight was measured, the abdominal part was shaved, and the rabbit was retained in a dorsal position.
(3) Continuous anesthesia (2% Ketalar, normal saline solution containing heparin at 20 U/mL) was administered from the ear vein.
(4) Median incision was performed from the immediately below the xiphoid process of the sternum to the lower abdomen for laparotomy.
(5) A heparin sodium injection solution at 300 U/kg was administered from the ear vein.
(6) Hepatic lobes (lateral left lobe, medial left lobe, and right lobe) having a thickness sufficient for making an injury were taken out using forceps for the intestine, gauze, and the like.
(7) A skin punch was used to make an injury having a diameter of 10 mm and a depth of 4 mm in the hepatic lobe, and the site was resected by a surgical knife.
(8) Bleeding from the resection wound was absorbed in Ben sheets for 10 seconds and the weight was measured. The wound from which bleeding was 0.5 g or more was used in the test.
(9) A layer composed of a water-soluble polymer and fibrinogen and a layer composed of an aliphatic polyester and thrombin that were each cut into 2.5×2.5 cm were placed in an overlapping manner on the wound site, wherein the layer composed of a water-soluble polymer and fibrinogen was applied on the bleeding site, and the bleeding site was pressed for 1 minute. In the case of TachoComb used as a control, it was cut into 2.5×2.5 cm, 312.5 µL of normal saline solution was added dropwise on the sheet and the bleeding site was pressed for 1 minute.
(10) After the pressing, the presence/absence of bleeding was observed and the bleeding from the wound site, which was absorbed in a Ben sheet, was weighed.

The results show that when the laminated formed sheet product according to the present invention was used, hemostasis occurred (n=1), the quantity of bleeding for 1 minute after application was quite small, 0.003 g. In the case of TachoComb (n=5) used as a control, the quantity of bleeding for 1 minute after application was 1.57 g, thus the hemostatic effect was insufficient and the quantity of bleeding was large.

Example 22

<Preparation of Formed Sheet Product Composed of an Aliphatic Polyester and Thrombin>

Lyophilized thrombin powder (recombinant thrombin 1 mg/mL, 3.4% sodium chloride, 1.2% sodium citrate, 0.29% calcium chloride, 1% mannitol at pH 7, which were lyophilized) was dispersed in ethanol, dichloromethane was added to the dispersion, and a polyglycolic acid-polylactic acid copolymer (Purasorb PDLG5010, Purac) was dissolved to make 10 mass % to prepare a spinning dope of lyophilized thrombin powder/polyglycolic acid-polylactic acid copolymer=100 (1.67 as thrombin)/100 (w/w). Spinning was conducted at a temperature of 22° C. and a humidity of 26% or lower by an electrospinning method to obtain a sheet-like formed fiber product. The inner diameter of the ejection nozzle was 0.8 mm, the voltage was 20 KV, the flow rate of the spinning dope was 4.0 mL/h, and the distance between the ejection nozzle and the earthed plate was 35 cm. The average fiber diameter of the formed fiber product obtained was 3.8 µm, the average thickness was 127 µm, the METSUKE was 1.38 mg/cm², and the bulk density was 109 mg/cm³. The formed sheet product obtained was cut into Φ1 cm, and protein was extracted using 200 µL of normal saline solution and subjected to measurement of thrombin activity (according to the method described in "8A. Measurement of thrombin activity"). As a result, the measured activity value was 18.3 U/cm².

Example 23

<Preparation of a Laminated Formed Sheet Product Composed of a Layer Composed of a Water-Soluble Polymer and Fibrinogen and a Layer Composed of an Aliphatic Polyester and Thrombin>

Lyophilized fibrinogen powder (recombinant fibrinogen 10 mg/mL, 10 mM arginine, 130 mM sodium chloride, 0.5% mannitol at pH 8.5, which were lyophilized) was ground by a mortar to prepare lyophilized fibrinogen powder having an average particle diameter of 30 µm. After this lyophilized fibrinogen powder was dispersed in 2-propanol, hydroxypropyl cellulose (2.0-2.9 mPa·s, Nippon Soda Co., Ltd.) and MACROGOL (molecular weight: 400, Sanyo Chemical Industries, Ltd.) were dissolved to make 15 mass % to prepare a dope liquid of lyophilized fibrinogen powder/hydroxypropyl cellulose/MACROGOL=51 (25.92 as fibrinogen)/34/15 (w/w/w). The dope liquid obtained was used and a film was prepared by casting. The coating distance was 127 µm and the coating speed was 30.1 mm/sec. The layer composed of an aliphatic polyester and thrombin prepared in Example 22 was laminated on the film within 1 minute after preparation of the film, to obtain a laminated formed sheet product composed of the layer composed of a water-soluble polymer and fibrinogen and the layer composed of an aliphatic polyester and thrombin to obtain a laminated formed sheet product. The laminated formed sheet product obtained had an average film thickness of 157 µm. The laminated formed sheet product obtained was sterilized by electron beam at 20 kGy. The laminated formed sheet product obtained was cut into Φ1 cm, protein was extracted using 200 µL of normal saline solution and subjected to ELISA assay for fibrinogen (according to the method described in "7A. ELISA assay (1) fibrinogen".). The results show that the amount of the fixed protein was 0.58 mg/cm$^2$.

Example 24

<Hemostatic Effect on Exudative Bleeding from the Liver of Rabbits>

The hemostatic effect of the laminated formed sheet product composed of a layer composed of a water-soluble polymer and fibrinogen and a layer composed of an aliphatic polyester and thrombin prepared in Example 23 was compared with the hemostatic effect of TachoSil.

Rabbits were used as an animal hemostasis model. A rabbit was lapatomized, a part of the liver was resected, a laminated formed sheet product composed of a layer composed of the water-soluble polymer and fibrinogen and a layer composed of an aliphatic polyester and thrombin was applied on the bleeding site, and the hemostatic effect (presence/absence of hemostasis, amount of bleeding) were observed. The test method was the same as that described in Example 21.

The results show that, when the laminated formed sheet product according to the present invention was used (n=4), the amount of bleeding for 1 minutes after application was very small, 0.003 g. On the other hand, with TachoSil (n=4) used as a control, the amount of bleeding for 1 minutes after application was 0.65 g and it was high, indicating that the hemostatic effect was insufficient.

Example 25

<Preparation of a Formed Sheet Product Composed of an Aliphatic Polyester and Thrombin>

Lyophilized thrombin powder (recombinant thrombin 1 mg/mL, 3.4% sodium chloride, 1.2% sodium citrate, 0.29% calcium chloride, 1% mannitol at pH 7, which was lyophilized) was dispersed in ethanol, then dichloromethane was added to the dispersion, and a polyglycolic acid-polylactic acid copolymer (Purasorb PDLG5010, Purac) was dissolved to make 10 mass % to prepare a spinning dope of lyophilized thrombin powder/polyglycolic acid-polylactic acid copolymer=100 (1.67 as thrombin)/100 (w/w). Spinning was conducted at a temperature of 22° C. and a humidity of 26% or lower by an electrospinning method to obtain a sheet-like formed fiber product. The inner diameter of the ejection nozzle was 0.8 mm, the voltage was 20 KV, the flow rate of the spinning dope was 4.0 mL/h, and the distance between the ejection nozzle and the earthed plate was 35 cm. The average fiber diameter of the formed fiber product obtained was 2.97 µm, the average thickness was 137 µm, the METSUKE was 1.49 mg/cm$^2$, and the bulk density was 108 mg/cm$^3$.

Example 26

<Preparation of a Laminated Formed Sheet Product Composed of a Layer Composed of a Water-Soluble Polymer and Fibrinogen and a Layer Composed of an Aliphatic Polyester and Thrombin>

Lyophilized fibrinogen powder (recombinant fibrinogen 10 mg/mL, 10 mM arginine, 130 mM sodium chloride, 0.5% mannitol at pH 8.5, which was lyophilized) was ground by a mortar to prepare ground lyophilized fibrinogen powder having an average particle diameter of 30 µm. After the ground lyophilized fibrinogen powder was dispersed in 2-propanol, hydroxypropyl cellulose (2.0-2.9 mPa·s, Nippon Soda Co., Ltd.) to make 2.9 mass % and MACROGOL (molecular weight: 400, Sanyo Chemical Industries, Ltd.) were dissolved to prepare a dope liquid of lyophilized fibrinogen powder/hydroxypropyl cellulose/MAC-ROGOL=90 (36.98 as fibrinogen)/7/3 (w/w/w). The dope liquid obtained was used to prepare a film by casting. The coating distance was 50.8 µm and the coating speed was 30.1 mm/sec. The layer composed of an aliphatic polyester and thrombin prepared in Example 25 was laminated onto the film within 1 minute after preparation of the film to obtain a laminated formed sheet product composed of a layer composed of a water-soluble polymer and fibrinogen and a layer composed of an aliphatic polyester and thrombin. The average film thickness of the laminated formed sheet product obtained was 169 µm. The laminated formed sheet product obtained was cut into Φ 0.5 cm, fibrinogen was extracted using a 0.1% TFA solution and quantified by high performance liquid chromatography (method described in "2D. Measurement of fibrinogen content"). The results show that the amount of the fixed protein was 0.54 mg/cm$^2$.

Example 27

<Hemostatic Effect on Exudative Bleeding of the Rabbit Liver>

The hemostatic effect of the laminated formed sheet product composed of a layer composed of a water-soluble polymer and fibrinogen and a layer composed of an aliphatic polyester and thrombin prepared in Example 26 was compared with the hemostatic effect of TachoSil.

Rabbits were used as an animal hemostasis model. A rabbit was lapatomized, a part of the liver was resected, a laminated formed sheet product composed of a layer composed of a water-soluble polymer and fibrinogen and a layer composed of an aliphatic polyester and thrombin was applied on the bleeding site and the hemostatic effects (presence/absence of hemostasis, amount of bleeding) were observed. The test method was the same as that described in Example 21.

The results show that, when the laminated formed sheet product according to the present invention was used (n=6), the amount of bleeding for 1 minutes after application was very small, 0.003 g. On the other hand, with TachoSil (n=4) used as a control as is shown in Example 24, the amount of bleeding for 1 minute after application was 0.65 g and it was high, indicating that the hemostatic effect was insufficient.

Example 28

Lyophilized fibrinogen powder (recombinant fibrinogen 10 mg/mL, 10 mM arginine, 110 mM sodium chloride, 1% glycine, 0.2% mannitol, 0.25% phenylalanine, 0.4% histidine, 0.1% trisodium citrate at pH 8.5, which was lyophilized) was ground by a mortar to prepare lyophilized fibrinogen powder having an average particle diameter of 22 µm. After the ground lyophilized fibrinogen powder was dispersed in 2-propanol, hydroxypropyl cellulose (2.0 to 2.9 mPa·s, Nippon Soda Co., Ltd.) was dissolved to make 4.2 mass % to prepare a dope liquid of lyophilized fibrinogen powder/hydroxypropyl cellulose/=90 (26.55 as fibrinogen)/10 (w/w). The dope liquid obtained was used to prepare a film by casting. The coating distance was 101.6 µm and the coating speed was 30.1 mm/sec. The sheet-like formed fiber products having proportions of lyophilized thrombin powder/polyglycolic acid-polylactic acid copolymer=20/100, 40/100, 60/100, 80/100, and 100/100 prepared by the method described in Example 25 were laminated onto the film within 3 minutes after preparation of the film to obtain a laminated formed sheet product composed of a layer composed of a water-soluble polymer and fibrinogen and a layer composed of an aliphatic polyester and thrombin. The hemostatic effect of these laminated formed sheet products was evaluated by the rat oozing model drug efficacy evaluation. In this evaluation test, an exudative bleeding rat model was used, wherein a wound was formed in the liver. The test formed sheet product was pressed on a wound site for a certain duration (5 minutes in this Example), and then the presence/absence of bleeding was visually observed for 1 minute. The test was conducted with n=6 to confirm the presence/absence of bleeding.

As a result, as shown in Table 1, the hemostatic effect exceeding that obtained by TachoSil was confirmed for the lyophilized thrombin powder/polyglycolic acid-polylactic acid copolymer in the evaluated proportion range of 20/100 to 100/100.

TABLE 1

| Thrombin/polymer | 20/100 | 40/100 | 60/100 | 80/100 | 100/100 | TachoSil |
|---|---|---|---|---|---|---|
| Thrombin content (U/cm$^2$) | 27.0 | 27.6 | 27.1 | 29.4 | 29.5 | |
| Fibrinogen content (mg/cm$^2$) | 0.67 | 0.55 | 0.58 | 0.55 | 0.58 | |
| Hemostasis rate (n = 6), number of sites where hemostasis was achieved/number of sites tested | 4/6 | 3/6 | 4/6 | 6/6 | 5/6 | 1/6 |
| Average bleeding amount (g) for 1 minute after hemostasis | 0.011 | 0.027 | 0.015 | 0.006 | 0.009 | 0.869 |

Example 29

Sheet-like formed fiber products having different thrombin contents (thrombin content 0.23 U/cm$^2$, 2.8 U/cm$^2$, 11.4 U/cm$^2$, and 28.5 U/cm$^2$) were obtained by the method described in Example 25. Then, a laminated formed sheet product composed of a layer composed of a water-soluble polymer and fibrinogen having a constant fibrinogen content and a layer composed of an aliphatic polyester and thrombin was prepared by the method described in Example 26. The test method is as follows:

(1) A laminated formed sheet product and a positive control preparation (TachoSil) (1 cm×cm) were adhered to the bottom of a plastic quadrangular prism (1 cm×1 cm) with a double-faced adhesive tape.
(2) The laminated formed sheet product and the positive control preparation (TachoSil) were immersed in 1 mL of normal saline solution for 10 seconds and firmly attached to a lauan plate.
(3) A load of 100 g was applied from above to the quadrangular prism for 5 minutes.
(4) The quadrangular prism was tracted at a speed of 30 mm/min and the tensile force was measured by a digital force gauge.

The test was conducted with n=5 and an average tensile force was evaluated as the adhesive strength (g). As a result, as shown in Table 2, all the laminated formed sheet products were excellent and exhibited a higher adhesive strength than TachoSil.

TABLE 2

| Thrombin content (U/cm$^2$) | 0.23 | 2.8 | 11.4 | 28.5 | TachoSil |
|---|---|---|---|---|---|
| Fibrinogen content (mg/cm$^2$) | 0.5 | 0.5 | 0.51 | 0.57 | |
| Adhesive strength (g) | 468.2 | 429.0 | 467.2 | 493.2 | 238.6 |

Example 30

A formed sheet product composed of an aliphatic polyester and thrombin (thrombin content of 24.2 U/cm$^2$) was obtained by the method described in Example 25, and the hemostatic effect of this formed sheet product was examined by the method described in Example 28 (pressing time of 3 minutes). The test was conducted with n=6. As a result, hemostasis was confirmed in all of the samples (6/6).

Example 31

A formed sheet product composed of an aliphatic polyester and thrombin (thrombin content range: 19 to 26 U/cm$^2$) was obtained by the method described in Example 25, and then a laminated formed sheet product composed of a layer composed of a water-soluble polymer and fibrinogen at various contents and a layer composed of an aliphatic polyester and thrombin were obtained by the method described in Example 26. The hemostatic effect of the obtained laminated formed sheet products having a thrombin content in a certain range and different fibrinogen contents was examined by the method described in Example 28. As a result, as shown in Table 3, a high hemostatic effect was confirmed for all fibrinogen contents, but the effect slightly decreased at 1.47 mg/cm².

TABLE 3

| Fibrinogen content (mg/cm²) | 0.28 | 0.55 | 1.16 | 1.47 |
|---|---|---|---|---|
| Confirmation of hemostasis | 5/6 | 5/6 | 4/6 | 2/6 |

INDUSTRIAL APPLICABILITY

The formed sheet product according to the present invention is used as a hemostatic material and can be utilized in the medical product manufacturing industry.

The invention claimed is:

1. A laminated formed sheet product comprising a first polymer composition layer comprising fibrinogen and a water-soluble polymer and a second polymer composition layer comprising thrombin and an aliphatic polyester, wherein at least part of said fibrinogen is incorporated into said water-soluble polymer and at least part of said thrombin is incorporated into said aliphatic polyester.

2. The laminated formed sheet product according to claim 1, wherein the water-soluble polymer is at least one selected from the group consisting of a cellulose derivative, a polymer having an N-vinyl cyclic lactam unit, polyethylene oxide, polyvinyl alcohol, hyaluronic acid, dextran, pullulan, starch, and a mixture thereof.

3. The laminated formed sheet product according to claim 1, wherein the water-soluble polymer is at least one selected from the group consisting of hydroxypropyl cellulose, methyl cellulose, hydroxyethyl cellulose, hydroxypropylmethyl cellulose, carboxymethyl cellulose sodium, and a mixture thereof.

4. The laminated formed sheet product according to claim 1, wherein the aliphatic polyester is at least one selected from the group consisting of polyglycolic acid, polylactic acid, polycaprolactone, a copolymer thereof, and a mixture thereof.

5. The laminated formed sheet product according to claim 1, wherein the first polymer composition layer contains at least one additive selected from the group consisting of blood coagulation factor XIII, albumin, isoleucine, glycine, arginine, glutamic acid, phenylalanine, histidine, a surfactant, sodium chloride, sugar alcohol, trehalose, sodium citrate, aprotinin, and calcium chloride.

6. The laminated formed sheet product according to claim 1, wherein the first polymer composition layer is composed of a formed film product or a formed fiber product.

7. The laminated formed sheet product according to claim 1, wherein the first polymer composition layer is composed of a formed film product.

8. The laminated formed sheet product according claim 7, wherein the formed film product has content of the water-soluble polymer of 0.1 to 50 mass %.

9. The laminated formed sheet product according to claim 7, wherein the formed film product contains fibrinogen at 0.05 to 10 mg/cm2.

10. The laminated formed sheet product according to claim 7, wherein formed film product is manufactured from a suspension composed of a water soluble polymer solution and fibrinogen powder.

11. The laminated formed sheet product according to claim 1, wherein the second polymer composition layer is composed of a formed fiber product.

12. The laminated formed sheet product according to claims 1 to 11, wherein the fibrinogen or a mixture of the fibrinogen and an additive(s) and/or thrombin or a mixture of the thrombin and an additive(s) is/are dispersed as protein particles in at least one polymer selected from the group consisting of an aliphatic polyester and a water-soluble polymer.

13. The laminated formed sheet product according to claim 12, wherein the hemostatic protein is thrombin.

14. The laminated formed sheet product according to claim 13, wherein a ratio by weight of the protein particles to the aliphatic polyester is 10:10 to 10:100.

15. The laminated formed sheet product according to claim 12, wherein the formed fiber product is manufactured from a suspension composed of an aliphatic polyester solution and thrombin powder.

16. A hemostatic material comprising the laminated formed sheet product according to claim 1.

17. A tissue adhesive material or tissue closure material comprising the laminated formed sheet product according to any of claim 1.

18. A method for treatment a wound site, comprising a step of applying the hemostatic material according to claim 16 onto the wound site.

19. A method for treatment a wound site, comprising a step of applying the tissue closure material according to claim 17 onto the wound site.

* * * * *